US012703674B2

(12) United States Patent
Kirilin et al.

(10) Patent No.: US 12,703,674 B2
(45) Date of Patent: Aug. 11, 2026

(54) PROCESSES FOR PRODUCING CARBOXYLIC ACIDS OR ALKYL ESTERS

(71) Applicant: Dow Global Technologies LLC, Midland, MI (US)

(72) Inventors: Alexey Kirilin, Terneuzen (NL); Beata A. Kilos, Midland, MI (US); Wen-Sheng Lee, Midland, MI (US); David G. Barton, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 429 days.

(21) Appl. No.: 18/568,913

(22) PCT Filed: Jun. 2, 2022

(86) PCT No.: PCT/US2022/031887

§ 371 (c)(1),
(2) Date: Dec. 11, 2023

(87) PCT Pub. No.: WO2023/009211

PCT Pub. Date: Feb. 2, 2023

(65) Prior Publication Data

US 2024/0286988 A1 Aug. 29, 2024

Related U.S. Application Data

(60) Provisional application No. 63/227,491, filed on Jul. 30, 2021.

(51) Int. Cl.

*C07C 51/10* (2006.01)
*B01J 27/043* (2006.01)
*B01J 35/37* (2024.01)
*B01J 35/61* (2024.01)
*B01J 37/08* (2006.01)

(52) U.S. Cl.

CPC ............. *C07C 51/10* (2013.01); *B01J 27/043* (2013.01); *B01J 35/613* (2024.01); *B01J 35/615* (2024.01); *B01J 35/617* (2024.01); *B01J 37/08* (2013.01); *B01J 35/37* (2024.01); *B01J 2235/00* (2024.01); *B01J 2235/15* (2024.01)

(58) Field of Classification Search

CPC ....... C07C 51/10; C07C 51/14; C07C 53/122; B01J 27/046; B01J 35/613; B01J 37/08; B01J 21/04; B01J 21/12; B01J 37/088

See application file for complete search history.

(56) References Cited

U.S. PATENT DOCUMENTS

| | | | |
|---|---|---|---|
| 1,924,767 | A | 8/1933 | Carpenter |
| 2,008,348 | A | 7/1935 | Carpenter |
| 2,089,903 | A | 8/1937 | Larson |
| 3,501,518 | A | 3/1970 | Kutepow et al. |
| 3,507,891 | A | 4/1970 | Hearne et al. |
| 4,287,050 | A | 9/1981 | Eastman et al. |
| 4,371,458 | A | 2/1983 | Eastman et al. |
| 4,389,304 | A | 6/1983 | Eastman et al. |
| 4,522,709 | A | 6/1985 | Aldag, Jr. et al. |
| 4,652,546 | A | 3/1987 | Aldag, Jr. et al. |
| 8,389,433 | B2 | 3/2013 | Mironov et al. |
| 9,938,226 | B2 | 4/2018 | Barton et al. |
| 10,144,693 | B2 | 12/2018 | Barton et al. |
| 2009/0057201 | A1 | 3/2009 | Brait et al. |
| 2018/0112139 | A1 | 4/2018 | Lin et al. |

FOREIGN PATENT DOCUMENTS

| | | |
|---|---|---|
| CA | 1163260 | 3/1984 |
| CN | 108745381 | 11/2018 |
| CN | 109985641 | 7/2019 |
| EP | 0065028 | 11/1982 |
| RU | 2677285 | 1/2019 |
| WO | 1999021820 | 5/1999 |
| WO | 2016154196 | 9/2016 |

OTHER PUBLICATIONS

Bhattacharyya, "Catalytic synthesis of ethyl propionate from ethylene, carbon monoxide and ethanol at high pressure", Brennstoff-Chemie, 1962, vol. 43, pp. 114-118.

Chetana, "TGA studies of metoclopramide complexes of cobalt(II) in the solid state", Termochimica Acta, 2005, vol. 425, pp. 13-21.

Hidai, "Synthesis of ketones and esters from olefins, carbon monoxide and alcohols by using ruthenium-iodide catalysts", J. Molecular Catalysis, 1987, vol. 40, pp. 243-254.

Robertson, "Unusual products from CO/ethene reactions catalysed by B-ketophosphine and related complexes of rhodium", Chem. Commun., 2001, pp. 47-48.

Samel, "Propionic acid and derivatives", Ullmann's Encyclopedia of Industrial Chemistry, 2012, vol. 30, pp. 295-311.

*Primary Examiner* — Jafar F Parsa

(57) ABSTRACT

The present invention relates generally to gas phase processes for producing carboxylic acids or alkyl esters. In one embodiment, a gas phase process for producing a carboxylic acid or an alkyl ester comprises (a) providing a catalyst support comprising deposits of cobalt thiocyanate on at least a portion of the catalyst support; (b) heating the catalyst support to convert the cobalt thiocyanate on the support to cobalt sulfide to form a supported cobalt sulfide catalyst; and (c) reacting alkene gas, steam or an alkanol gas, and a carbon-containing gas in the presence of the supported cobalt sulfide catalyst in a reactor to form a product stream, wherein the carbon-containing gas comprises carbon monoxide or a mixture of carbon monoxide and carbon dioxide, wherein when steam is used as a reactant, the product stream comprises a carboxylic acid, and wherein when alkanol gas is used as a reactant, the product stream comprises an alkyl ester.

15 Claims, No Drawings

PROCESSES FOR PRODUCING CARBOXYLIC ACIDS OR ALKYL ESTERS

FIELD

The present invention relates generally to gas phase processes for producing carboxylic acids or alkyl esters.

BACKGROUND

Carboxylic acids, such as propionic acid, are important intermediates for the synthesis of a number of oxygenates that find applications in herbicides, food preservatives, plastics, plasticizers, and cosmetics.

Various methods are known for the production of carboxylic acids. Taking as an example propionic acid, one commercial process relies on the liquid phase hydrocarboxylation of ethylene. In this process, ethylene, carbon monoxide (CO), and water are converted directly into propionic acid in the presence of a highly toxic $Ni(CO)_4$ catalyst at harsh reaction conditions (e.g., 250-320° C. and 100-300 bar).

A second liquid phase method to produce carboxylic acids uses olefin hydroformylation, followed by oxidation of the aldehyde to produce the carboxylic acid. In this commercially practiced, two reaction step, process to produce propionic acid, propanal is produced in the first step via the hydroformylation of ethylene, and in a second step propanal is oxidized to propionic acid ("Ullmann's Encyclopedia of Industrial Chemistry" Vol. 30, pp. 295-311 (2012)).

Another route to produce carboxylic acids is the direct oxidation of hydrocarbons ("Ullmann's Encyclopedia of Industrial Chemistry" Vol. 30, pp. 295-311 (2012)). Direct oxidation of hydrocarbons can also be used to produce propionic acid as a by-product during acetic acid synthesis from naphtha ("Ullmann's Encyclopedia of Industrial Chemistry" Vol. 30, pp. 295-311 (2012)).

The liquid phase single-step hydrocarboxylation of ethylene has an advantage in ethylene yield compared to the two-step hydroformylation/oxidation route; however, it has found limited industrial use because of the cost and risk associated with operating a high pressure reactor that uses a corrosive and toxic nickel carbonyl catalyst.

The processes listed above refer to reactions in the liquid phase. The open literature on gas phase hydrocarboxylation is limited. Early work described the formation of a carboxylic acid via mixing steam with CO and an olefin. Examples of catalysts are charcoal (see U.S. Pat. No. 2,089,903), ZnCl (see U.S. Pat. No. 1,924,767) and tungsten oxides (see U.S. Pat. No. 2,008,348), and in all cases the catalysts were used in combination with metal halides. Although these works indicate a pressure range between 25 and 900 atm, the examples are performed at 600-700 atm.

U.S. Pat. No. 3,501,518 discloses that the carbonylation reaction can by activated by Pd sulfide. The reaction is performed in the liquid phase at a temperature range of 30-180° C. at a pressure of 5-100 MPa (49-987 atm) and requires the addition of halides or co-catalysts such as acids and an organic phosphine or nitrile.

Recently, U.S. Pat. No. 10,144,693 disclosed an improved gas phase hydrocarboxylation process with Group VIII metal sulfide catalysts. This included bulk and supported catalysts which allow high propionic acid selectivity. U.S. Pat. No. 10,144,693 also described methods of preparing cobalt sulfide catalysts.

Alkyl esters, such as methyl propionate, n-propyl propionate, n-butyl propionate, and n-pentyl propionate, are important for solvents that find application in lacquers, inks, paints, coatings, films, and fragrances, among other uses.

Various methods are known for the production of alkyl esters of aliphatic carboxylic acids, e.g., methyl methacrylate (MMA). One commercial method relies solely on acetone cyanohydrin (ACH) technology, i.e., the reaction of acetone with hydrogen cyanide to form ACH followed by acid-assisted hydrolysis and esterification with methanol to produce approximately 400 kilo-tons annually of MMA. Although the ACH route has traditionally been a core technology used in the United States and other parts of the world, lower cost alternative technologies are under consideration for future capacity increases. Several of these alternative technologies are ethylene-based. One such method is the hydroformylation of ethylene-to-propionaldehyde, followed by condensation to form methacrolein (MA) and subsequent oxidation and esterification to form MMA. Another route is the Alpha process which is a two-step, liquid phase process that uses a homogeneous palladium-based catalyst to make methyl propionate which is then condensed with formaldehyde in a second step to make MMA. The process is described in PCT Publication No. WO1999/021820. Other reports of homogenous catalysts for the liquid phase carbonylation of ethylene to methyl propionate include U.S. Pat. No. 3,507,891 (cobalt-pyridine catalyst), Chem. Commun., 2001, 47-48 (rhodium/b-ketophosphine catalyst); and J. Molecular Catalysis 40 (1987) 243-254, Hidai et al. (ruthenium-iodide catalyst).

One report of a heterogeneous catalyst that operates in the gas phase is by Bhattacharyya, S. K. and Nag, S. N., Brennstoff-Chemie, Vol. 43, p. 114-118 (1962). This work describes the use of metal iodides supported on silica gel for the synthesis of methyl propionate from ethylene, CO, and methanol in the gas phase. This process produces a large amount of undesirable by-product oxygenates and hydrocarbon compounds, and operates at a pressure of 253 bar (25.3 MPa).

Recently, U.S. Pat. No. 9,938,226 disclosed a gas phase carbonylation process for making alkyl alkanoates using Group VIII metal sulfide catalysts. U.S. Pat. No. 9,938,226 also described methods of preparing cobalt sulfide catalysts.

In addition to the processes for preparing cobalt sulfide catalysts described in U.S. Pat. Nos. 9,938,226 and 10,144,693, there have been alternative approaches to preparing cobalt sulfide catalysts such as described in EP0065028A1 and Thermochimica Acta 425 (2005), pp. 13-21, which employ additional organic ligands and/or air oxidation; such approaches can, however, lead to undesired Co-oxides. RU 2677285 uses CoO and attempts to convert the oxide to the sulfide with hydrogen gas.

It would be desirable to have alternative gas phase processes for producing carboxylic acids and/or alkyl esters.

SUMMARY

Embodiments of the present invention advantageously provide alternative gas phase processes for producing carboxylic acids and/or alkyl esters. Such processes utilize a supported cobalt sulfide catalyst prepared in a manner that provides a number of advantages. For example, the process is versatile and can enable, in some embodiments, preparation of the catalyst using a variety of supports, such as $Al_2O_3$, $SiO_2$, carbon, and SiC. In some embodiments, the carbonylation reaction surprisingly can proceed using the cobalt sulfide catalyst with no need for a halide, or other co-catalyst, and can proceed at moderate pressures. In some embodiments, the cobalt sulfide catalysts can show promising performance in the direct propionic acid synthesis achieving high selectivity >98% and productivity comparable to or exceeding that of prior bulk cobalt sulfide catalysts.

In one aspect, a gas phase process for producing a carboxylic acid or an alkyl ester comprises:

(a) providing a catalyst support comprising deposits of cobalt thiocyanate on at least a portion of the catalyst support, wherein the catalyst support has a surface area of greater than 5 $m^2/g$;

(b) heating the catalyst support to convert the cobalt thiocyanate on the support to cobalt sulfide to form a supported cobalt sulfide catalyst; and (c) reacting alkene gas, steam or an alkanol gas, and a carbon-containing gas in the presence of the supported cobalt sulfide catalyst in a reactor to form a product stream, wherein the carbon-containing gas comprises carbon monoxide or a mixture of carbon monoxide and carbon dioxide, wherein when steam is used as a reactant, the product stream comprises a carboxylic acid, and wherein when alkanol gas is used as a reactant, the product stream comprises an alkyl ester.

These and other embodiments are described in more detail in the Detailed Description.

DETAILED DESCRIPTION

This disclosure relates generally to gas phase processes for producing carboxylic acids or alkyl esters. The processes utilize supported cobalt sulfides that are prepared in a manner that provides a number of advantages. In general, a catalyst support is provided with deposits of cobalt thiocyanate on at least a portion thereof, and then heated to convert the cobalt thiocyanate on the support to cobalt sulfide and form a supported cobalt sulfide catalyst. As described further herein, such supported cobalt sulfide catalysts perform well in the synthesis of carboxylic acids and alkyl esters achieving high selectivity and productivity, particularly when compared to prior bulk cobalt sulfide catalysts.

All references to the Periodic Table of the Elements refer to the Periodic Table of the Elements published at page 1-10 of the CRC Handbook of Chemistry and Physics, 71$^{st}$ Ed. (1990-1991). Also, any references to a Group or Groups shall be to the Group or Groups reflected in this Periodic Table of the Elements using the IUPAC system for numbering groups. Unless stated to the contrary, implicit from the context, or customary in the art, all parts and percentages are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, weight percentages, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amounts of the various reactants in and the operating conditions of the inventive process.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

As used herein, the term "ppmw" means parts per million by weight. When used to assess concentration of weakly basic amine, the phrase "ppmw (by nitrogen)" is based on the weight of the amine nitrogen divided by the total weight of the mixture. This makes the analysis independent of the molecular weight of the amine and focuses on the active group on the weakly basic amine. The amine nitrogen does not include nitrogen moieties not capable of reacting with acids such as quaternary amines.

"Composition" and like terms mean a mixture or blend of two or more components.

"Hydroxycarbonylation conditions" and like terms mean the temperature, pressure and other conditions necessary for an alkene, carbon monoxide and water, one or more of which is at least partially in the form of a gas, to react with one another over and in contact with a solid sulfide containing catalyst to form a carboxylic acid. In one embodiment, each of the alkene, CO, and water are at least partially in the form of a gas. In one embodiment, each of the alkene, CO, and water are completely or nearly completely in the form of a gas.

"Halogen-free hydroxycarbonylation conditions" and like terms mean hydroxycarbonylation conditions in which halogen in any form is absent or essentially absent from the space in which the alkene, CO, and water are contacted over a sulfide containing catalyst to form a carboxylic acid. "Essentially absent" means, in the context of a halogen, that any halogen present in the reaction space is present in an amount that does not materially affect the conversion or selectivity of the reactants to the desired carboxylic acid. The source of such halogen can be, for example, from one or more of the feeds to the reaction or the catalyst (as, for example, a contaminant), or from the surface of a piece of equipment, etc. In one embodiment "halogen-free" means less than 1000 parts per million (ppm), preferably less than 10 ppm, and more preferably less than 1 ppm, based on the combined weight of the reactants.

"Carbonylation conditions" and like terms mean the temperature, pressure and other conditions necessary for an alkene, carbon monoxide, and an alkanol, one or more of which is at least partially in the form of a gas, to react with one another over and in contact with a solid sulfide containing catalyst to form an alkyl alkanoate. In one embodiment each of the alkene, CO, and alkanol are at least partially in the form of a gas. In one embodiment each of the alkene, CO and alkanol are completely or nearly completely in the form of a gas.

"Halogen-free carbonylation conditions" and like terms mean carbonylation conditions in which halogen in any form is absent or essentially absent from the space in which the alkene, CO, and alkanol are contacted over a sulfide containing catalyst to form an alkyl alkanoate. "Essentially absent" means that any halogen present in the reaction space is present in an amount that does not materially affect the conversion or selectivity of the reactants to the desired alkyl alkanoate. The source of such halogen can be, for example, from one or more of the feeds to the reaction or the catalyst (as, for example, a contaminant), or from the surface of a piece of equipment, etc. In one embodiment "halogen-free" means less than 1000 parts per million (ppm), preferably less than 10 ppm and more preferably less than 1 ppm based on the combined weight of the reactants.

"Condensation conditions" and like terms mean the temperature, pressure and other conditions necessary for an alkyl alkanoate and an aldehyde, each in the form of a gas, to react with one another over and in contact with a solid condensation catalyst to form an alkyl ester of an aliphatic carboxylic acid.

In one aspect, a gas phase process for producing a carboxylic acid or an alkyl ester comprises (a) providing a catalyst support comprising deposits of cobalt thiocyanate on at least a portion of the catalyst support, wherein the catalyst support has a surface area of greater than 5 $m^2$/g; (b) heating the catalyst support to convert the cobalt thiocyanate on the support to cobalt sulfide to form a supported cobalt sulfide catalyst; and (c) reacting alkene gas, steam or an alkanol gas, and a carbon-containing gas in the presence of the supported cobalt sulfide catalyst in a reactor to form a product stream, wherein the carbon-containing gas comprises carbon monoxide or a mixture of carbon monoxide and carbon dioxide, wherein when steam is used as a reactant, the product stream comprises a carboxylic acid, and wherein when alkanol gas is used as a reactant, the product stream comprises an alkyl ester.

In some embodiments, the catalyst support comprising deposits of cobalt thiocyanate on at least a portion of the catalyst support is formed by contacting an aqueous solution of cobalt (II) salt in the presence of thiocyanate anion with a catalyst support to deposit the aqueous solution on at least a portion of the catalyst support. Thus, in some embodiments, the process further comprises contacting an aqueous solution of cobalt (II) salt in the presence of thiocyanate anion with a catalyst support to deposit the aqueous solution on at least a portion of the catalyst support and form the catalyst support comprising deposits of cobalt thiocyanate. In some embodiments, the cobalt (II) salt in the presence of thiocyanate anion is provided by first dissolving cobalt thiosulfate in water. In such embodiments, the process further comprises dissolving cobalt thiosulfate in water to provide the aqueous solution of cobalt (II) salt in the presence of thiocyanate anion. This is particularly advantageous over providing one compound with cobalt and another compound with thiocyanate as such an approach would require removal of the anion associated with cobalt and the cation associated with thiocyanate. In some embodiments, the aqueous solution does not include more than 0.1 molar equivalents of cations other than cobalt (II) relative to cobalt, and wherein the aqueous solution does not include more than 0.1 molar equivalents of anions other than thiocyanate anion relative to thiocyanate.

When the catalyst support is heated to convert the cobalt thiocyanate on the support to cobalt sulfide to form the supported cobalt sulfide catalyst, in some embodiments, the catalyst support is heated at a temperature between 200° C. and 550° C.

In some embodiments, processes of the present invention further comprises drying the catalyst support comprising deposits of cobalt thiocyanate on at least a portion of the catalyst support under inert conditions at a temperature of 150° C. or less prior to heating the catalyst support to convert the cobalt thiocyanate on the support to cobalt sulfide to form a supported cobalt sulfide catalyst.

In some embodiments, the catalyst support is heated to convert the cobalt thiocyanate on the support to cobalt sulfide to form a supported cobalt sulfide catalyst outside the reactor, and the process further comprises adding the supported cobalt sulfide catalyst to the reactor. In other embodiments, the catalyst support is heated in the reactor to convert the cobalt thiocyanate on the support to cobalt sulfide to form a supported cobalt sulfide catalyst.

In some embodiments, processes of the present invention further comprise passivating the supported cobalt sulfide catalyst with a diluted oxygen stream comprising up to 2 volume percent $O_2$ at a temperature of 25° C. or less. In some embodiments, such as where the supported cobalt sulfide catalyst is formed in the reactor, a passivation step may not be needed.

In some embodiments, the alkene gas is ethylene.

In some embodiments, processes of the present invention are continuous.

In some embodiments wherein the product stream comprises carboxylic acid, the carboxylic acid selectivity is equal to or greater than 80 mol %. In some embodiments wherein the product stream comprises an alkyl ester, the alkyl ester selectivity is equal to or greater than 80 mol %.

In some embodiments, the reaction to form the carboxylic acid or alkyl ester (e.g., reacting alkene gas, steam or an alkanol gas, and a carbon-containing gas in the presence of the supported cobalt sulfide catalyst to form a product stream) occurs in a reactor at a pressure of 0.1 MPa to 10 MPa.

Supported Cobalt Sulfide Catalyst

The catalyst used in gas phase processes of the present invention is a supported metal sulfide catalyst.

The supported cobalt sulfide catalyst used in embodiments of the present invention can advangeously be made by first forming a catalyst support comprising deposits of cobalt thiocyanate on at least a portion of the catalyst support. A variety of catalyst supports can be used in various embodiments. In general, a catalyst support should have sufficient mechanical strength and surface properties for use in the reaction conditions described herein. With regard to mechanical strength, in some embodiments, the catalyst support has a crush strength of greater than 2 pounds per millimeter. Regarding surface area, the catalyst support has a surface area of 5 $m^2$/gram or greater. In some embodiments, the catalyst support has a surface area of 10 $m^2$/gram or greater in some embodiments, 50 $m^2$/gram or greater in preferred embodiments, and 100 $m^2$/gram or greater in more preferred embodiments. In some embodiments, the surface area of the catalyst support is from greater than 10 $m^2$/g and up to 800 $m^2$/g. As used herein, the surface area of the catalyst support is measured by nitrogen adsorption at 77.4 K using the conventional technique on a Micromeritics ASAP 2420 apparatus. Prior to the adsorption measurements, the samples are degassed in vacuum at 300° C. for at least 3 hours. The surface area is calculated using BET method as known to those having ordinary skill in the art.

In some embodiments, the catalyst support can be alumina, carbon, silicon carbide, silica, silica-alumina, halfnia, zirconia, titania, and mixtures thereof.

The catalyst support is then contacted with an aqueous solution of cobalt (II) salt in the presence of thiocyanate anion to deposit the aqueous solution on at least a portion of the catalyst support. In some embodiments, cobalt thiosulfate is first dissolved in water to provide the aqueous solution of cobalt (II) salt in the presence of thiocyanate anion that is contacted with the catalyst support.

The cobalt (II) salt in the presence of thiocyanate anion is provided by first dissolving cobalt thiosulfate in water. In such embodiments, the process further comprises dissolving cobalt thiosulfate in water to provide the aqueous solution of cobalt (II) salt in the presence of thiocyanate anion. This is particularly advantageous over providing one compound with cobalt and another compound with thiocyanate as such an approach would require removal of the anion associated with cobalt and the cation associated with thiocyanate.

Once contacted with the aqueous solution of cobalt (II) salt in the presence of thiocyanate anion, the coated catalyst support can be dried to remove substantially all of the water. For example, in some embodiments, the coated catalyst support can be dried under inert conditions for 2 to 5 hours at temperatures of less than 150° C. Once dried, the catalyst support comprises deposits of cobalt thiocyanate on at least a portion of the catalyst support.

The catalyst support comprising deposits of cobalt thiocyanate is then heated to convert the cobalt thiocyanate on the support to cobalt sulfide to form a supported cobalt sulfide catalyst. In some embodiments, the catalyst support is heated at a temperature between 200° C. and 550° C. to convert the cobal thiocyanate to cobalt sulfide. In some embodiments, the catalyst support is heated to convert the cobalt thiocyanate on the support to cobalt sulfide in the flow of inert gas at a temperature between 200° C. and 550° C. In some embodiments, the catalyst support can be heated in the reactor (where carboxylic acid or alkyl ester is formed) to convert the cobalt thiocyanate on the support to cobalt sulfide. In other embodiments, the catalyst support can be heated outside the reactor, and then provided to the reactor at the appropriate time for use in the reaction.

In some embodiments, processes of the present invention further comprise passivating the supported cobalt sulfide catalyst with a diluted oxygen stream comprising up to 2 volume percent $O_2$ at a temperature of 25° C. or less. Passivating the supported cobalt sulfide catalyst can help avoid over oxidation of the cobalt sulfide particles and protect the catalyst prior to use. In some embodiments, such as where the supported cobalt sulfide catalyst is formed in the reactor, a passivation step may not be needed.

The cobalt sulfide can comprise a number of phases. In some embodiments, the cobalt sulfide comprises $CoS_2$, $Co_4S_3$, $Co_3S_4$, CoS, $Co_7S_8$, $Co_9S_8$, $Co_{1-x}S$ where x is less than or equal to 0.2, or combinations thereof. While much of the cobalt sulfide on the catalyst support may be crystalline, in some embodiments, at least a portion of the cobalt sulfide may be amorphous.

In some embodiments, the catalyst support comprises alumina, carbon, silicon carbide, silica, silica-alumina, halfnia, zirconia, titania, or mixtures thereof.

In some embodiments, the bulk sulfur-to-cobalt atomic ratio in the cobalt sulfide is equal or greater than 0.3. In some embodiments, the bulk sulfur-to-cobalt atomic ratio in the cobalt sulfide is equal or greater than 0.75. In some embodiments, the bulk sulfur-to-cobalt atomic ratio in the cobalt sulfide is up to 2.0.

In some embodiments, the cobalt content in the supported cobalt sulfide catalyst is between 5 weight percent and 50 weight percent, based on the total weight of the supported cobalt sulfide catalyst.

In some embodiments, the cobalt oxide content in the supported cobalt sulfide catalyst is less than 5 weight percent based on the total content of cobalt oxide and cobalt sulfide.

Production of Carboxylic Acids

Reactants

In the production of carboxylic acids according to some embodiments of the gas phase processes of the present invention, the reactants are alkene gas, steam (i.e., gaseous water), and a carbon-containing gas, wherein the carbon-containing gas comprises carbon monoxide or a mixture of carbon monoxide and carbon dioxide. The alkene gas can be either mono-, or polyolefinic, i.e., containing more than one double bond. The mono-olefinic alkene is of the formula $C_nH_{2n}$ in which n is an integer greater than 1, typically 2-8 and more typically 2-6. In some embodiments, n is 2 (i.e., the alkene is ethylene). Mixtures of alkenes may be employed in some embodiments. For example, commercial alpha olefins containing four or more carbon atoms may contain minor amounts of corresponding internal olefins and/or their corresponding saturated hydrocarbon and that such commercial alkenes need not necessarily be purified from same prior to use.

The carbon-containing gas can be carbon monoxide or a mixture of carbon monoxide and carbon dioxide. In some embodiments, the carbon-containing gas is carbon monoxide. In such embodiments, carbon monoxide can be used neat or in combination with one or more other gases that are inert with the reaction reagents, products, and by-products under reaction conditions. Such other gases include, but are not limited to, nitrogen and the noble gases.

The terms "alkene" and "olefin" are used interchangeably herein. Illustrative alpha and internal olefins include, for example, ethylene, propylene, 1-butene, 1-pentene, 1-hexene, 1-octene, 2-butene, 2-methyl propene (isobutylene), 2-methylbutene, 2-pentene, 2-hexene, 3-hexene, 2-heptene, cyclohexene, butadiene, styrene, 1,4-hexadiene, 1,7-octadiene, as well as alkyl alkenoates, alkenyl alkanoates, alkenyl alkyl ethers, alkenols, alkenals, and the like. Like the carbon monoxide, the alkene may comprise other compounds, such as impurities and contaminants. In the case of the alkene, some of these compounds may be present as a result of the process in which the alkene was formed. For example, a methane-containing source, such as shale gas or natural gas, can be converted to an alkene via techniques well-known to those skilled in the art. Depending on the alkene production process, by-products such as CO, $H_2$, $CO_2$, and/or others can be present in the alkene. Thus, in some embodiments, gas phase processes of the present invention comprise producing a carboxylic acid by contacting at a temperature of from more than 250° C. to 400° C. under halogen-free hydroxycarbonylation conditions an alkene gas, carbon monoxide gas, steam, and a supported cobalt sulfide catalyst, with the proviso that the alkene, preferably ethylene, is derived from a methane-containing source, such as shale gas or natural gas.

Water (liquid or gaseous) can be pure or diluted. In some embodiments, the water can be provided at least partially by any precursor that provides water, including alcohols, acids and other oxygenates.

Catalyst

The catalyst used in the reaction is the supported cobalt sulfide catalyst described above.

Process Conditions and Equipment

The processes of the present invention are conducted in the gas phase over a solid catalyst. As such, in one embodiment, the alkene, carbon-containing gas (e.g., CO) and water are introduced as gases and contacted with one another over and in contact with a solid catalyst bed. The reactants can be introduced in a single or multiple feed streams. In embodiments where the carbon-containing gas comprises carbon monoxide, the molar ratio of CO to alkene is typically at least 1:1, typically at least 3:1, more typically from 3:1 to 50:1 and even more typically from 3:1 to 15:1. The molar ratio of alkene to steam is typically at least 0.1:1, more typically at least 0.5:1, more typically from 0.1:1 to 10:1 and even more typically from 0.2:1 to 2:1.

Although the process can be operated in either a continuous or batch mode, the process is preferably operated in a continuous mode.

The process temperature can be from over 250° C. to 450° C., from 260° C. to 400° C., or from 280° C. to 350° C. The total pressure of the process can be from 0.1 to 30 MPa, or from 1.5 to 6 MPa. The gas hourly space velocity of the process is typically from 100 to 1,000,000 liters of gas feed per liter of catalyst per hour (L/L*h), more typically from 500 to 5,000 L/L*hr.

In one embodiment, the reaction is conducted in a fixed-bed reactor. In one embodiment the reactor is a tube reactor. In a typical protocol, the temperature and pressure are slowly increased to the reaction conditions. The catalyst can be exposed to a feed comprising an inert gas (such as nitrogen or helium), carbon monoxide, alkenes, water, optionally a small amount of a sulfur-containing gas, such as $H_2S$, and any combination of the above. Examples of other sulfur-containing gases include but are not limited to mercaptans, thiophenes, dimethyl sulfide and dimethyl disulfide. The feed gas may also include impurities or contaminants such as, for example, hydrogen. The effluent gas from the reactor can be analyzed via gas chromatography (GC) to determine the product composition and the amount of CO converted.

Production of Alkyl Esters

Reactants

In the production of alkyl esters according to some embodiments of the gas phase processes of the present invention, the reactants are alkene gas, an alkanol gas, and a carbon-containing gas, wherein the carbon-containing gas comprises carbon monoxide or a mixture of carbon monoxide and carbon dioxide. The alkene gas is of the formula $C_nH_{2n}$ in which n is an integer greater than (>) 1, typically 2-8 and more typically 2-6. In some embodiments, n is 2 (i.e., the alkene is ethylene). Mixtures of alkenes may be employed in some embodiments. For example, commercial alpha olefins containing four or more carbon atoms may contain minor amounts of corresponding internal olefins and/or their corresponding saturated hydrocarbon and that such commercial alkenes need not necessarily be purified from same prior to use.

The carbon-containing gas can be carbon monoxide or a mixture of carbon monoxide and carbon dioxide. In some embodiments, the carbon-containing gas is carbon monoxide. In such embodiments, carbon monoxide can be used neat or in combination with one or more other gases that are inert with the reaction reagents, products, and by-products under reaction conditions. Such other gases include, but are not limited to, nitrogen and the noble gases.

The alkanol (i.e., alcohol) gas is typically a $C_{1-8}$ alkanol which may contain one or more substituents such as a cyano, carbonyl, alkoxy or aryl group. Illustrative alkanols include, but are not limited to, methanol, ethanol, propanol, 2-propanol, 2-butanol, t-butyl alcohol and capryl alcohol. For purposes of this invention, polyhydroxyl compounds such as diols and sugars, are considered alkanols that can be used in the practice of this invention. Methanol is the is a particularly useful alkanol in some embodiments.

Catalyst

The catalyst used in the reaction is the supported cobalt sulfide catalyst described above.

Process Conditions and Equipment

The processes of the present invention are conducted in the gas phase over a solid catalyst. As such, in one embodiments, the alkene, carbon-containing gas (e.g., CO), and alkanol are introduced as gases and contacted with one another over and in contact with a solid catalyst bed. The reactants can be introduced in a single or multiple feed streams. In embodiments where the carbon-containing gas comprises carbon monoxide, the molar ratio of CO to alkene is typically at least 1:1, typically at least 3:1, more typically from 3:1 to 50:1 and even more typically from 3:1 to 15:1. The molar ratio of alkene to alkanol is typically at least 0.1:1, more typically at least 0.5:1, more typically from 0.1:1 to 10:1 and even more typically from 0.2:1 to 2:1.

Although the process can be operated in either a continuous or batch mode, the process is typically and preferably operated in a continuous mode.

The process temperature is typically from 120° C. to 450° C., more typically from 250° C. to 380° C. and even more typically from 280° C. to 340° C. The total pressure of the process is typically from 0.1 to 20 MPa, more typically from 1.5 to 6 MPa. The space velocity of the process is typically from 100 to 1,000,000 liters of gas feed per liter of catalyst per hour (L/L*h), more typically from 500 to 5,000 L/L*hr.

In one embodiment the reaction is conducted in a high-pressure, fixed-bed reactor. In one embodiment the reactor is a tube reactor. In a typical protocol the temperature and pressure is slowly increased to the reaction conditions. The catalyst can be exposed to a feed consisting of an inert gas (such as nitrogen or helium), hydrogen, small amount of $H_2S$, carbon monoxide, olefins, alkanols and any combination of the above. The effluent gas from the reactor is analyzed via gas chromatography (GC) to determine product composition and amount of CO converted.

In one embodiment of a gas phase process of the present invention, ethylene, CO, and methanol are contacted at carbonylation conditions and over and in contact with the supported cobalt sulfide catalyst to form methyl propionate.

Production of Alkyl Esters of Aliphatic Carboxylic Acids

In one embodiment of the invention, the alkyl ester made in the gas phase process described above is condensed with an aldehyde to form an alkyl ester of an aliphatic carboxylic acid. When the alkyl ester is methyl propionate and the aldehyde is formaldehyde, the product is methyl methacrylate (MMA). The equipment, conditions and protocol of this condensation reaction are well known to those of skill in the art.

Some embodiments of the invention will now be described in more detail in the following Examples.

EXAMPLES

All parts and percentages in the following examples are by weight unless otherwise indicated. Pressures are given as absolute pressure unless otherwise indicated.

Synthesis of Catalysts

A number of catalysts are synthesized as described. The catalysts described as Inventive Examples can be used in gas phase processes according to some embodiments of the present invention.

Inventive Example 1

Catalyst $Co_xS_y/Al_2O_3$ is prepared by an incipient wetness impregnation method. An impregnation solution of cobalt (II) thiocyanate in deionized water is prepared with concentration of 2 Molar. Then, 7.86 grams of 40-80 mesh size $Al_2O_3$ support (NORPRO SA31132) are placed in a porcelain dish and 7.86 milliliters of the impregnation solution are added dropwise while gently shaking. The properties of the support are provided in Tables 1a-1b.

In Tables 1a-1b, the surface area of the supports are measured by nitrogen adsorption at 77.4 K using the conventional technique on a Micromeritics ASAP 2420 apparatus. Prior to the adsorption measurements, the samples are degassed in vacuum at 300° C. for at least 3 hours.

The surface area is calculated using BET method as known to those having ordinary skill in the art.

The porcelain dish with impregnated catalyst is placed in a stainless steel drum where the catalysts are dried and autoreduced in the flow of pure $N_2$ (overhead flow 5.5 L/min) using the following procedure: flush with $N_2$ flow for 30 min at room temperature, increase from room temperature to 120° C. at 2° C./min, dwell at 120° C. for 2 h, increase from 120 to 550° C. at 3° C./min, dwell at 550° C. for 4 h, cool down to room temperature 20-25° C. (24 h-48 h). The catalyst is then passivated in 1 vol % $O_2/N_2$ flow for 2 hours at room temperature (20-25° C.), and then the oxygen concentration in the gas flow is gradually increased to 21 vol % $O_2/N_2$. The catalyst is purged for 1 hour in 21 vol % $O_2/N_2$ prior to opening the stainless steel drum. The result is black material. The catalyst composition is determined by X-ray fluorescence (XRF) and X-ray diffraction (XRD) and is reported in Tables 2a-2b.

Inventive Example 2

Catalyst $Co_xS_y/Al_2O_3$ is prepared by an incipient wetness impregnation method. The support is $Al_2O_3$(NORPRO SA6173; support properties are reported in Tables 1a-1b). The support is crushed and sieved to 40-80 mesh size. The same catalyst preparation method is used as was used in Inventive Example 1. The mass of support used is 9.14 grams. The volume of the 2M cobalt (II) thiocyanate solution used for incipient wetness impregnation is 8.226 milliliters. The catalyst composition is determined by XRF and XRD and is reported in Tables 2a-2b.

Inventive Example 3

Catalyst $Co_xS_y/Al_2O_3$ is prepared by an incipient wetness impregnation method. The support is $Al_2O_3$ (NORPRO SA6178; support properties are reported in Tables 1a-1b). The support is crushed and sieved to 40-80 mesh size. The same catalyst preparation method is used as was used in Inventive Example 1. The mass of support used is 6.8 grams. The volume of the 2M cobalt (II) thiocyanate solution used for incipient wetness impregnation is 5.916 milliliters. The catalyst composition is determined by XRF and XRD and is reported in Tables 2a-2b.

Inventive Example 4

Catalyst $Co_xS_y/Al_2O_3—SiO_2$ is prepared by an incipient wetness impregnation method. The support is $Al_2O_3—SiO_2$ (SASOL Siralox 1.5/140 in the powder form; support properties are reported in Tables 1a-1b). The same catalyst preparation method is used as was used in Inventive Example 1. The mass of support used is 10 grams. The volume of the 2M cobalt (II) thiocyanate solution used for incipient wetness impregnation is 9.5 milliliters. After preparation, the catalyst was pelletized, crushed and sieved to 40-80 mesh size. The catalyst composition is determined by XRF and XRD and is reported in Tables 2a-2b.

Inventive Example 5

Catalyst $Co_xS_y/Al_2O_3$ is prepared by an incipient wetness impregnation method. The support is $Al_2O_3$(NORPRO SA6176; support properties are reported in Tables 1a-1b). The support is crushed and sieved to 40-80 mesh size. The same catalyst preparation method is used as was used in Inventive Example 1. The mass of support used is 10 grams. The volume of the 2M cobalt (II) thiocyanate solution used for incipient wetness impregnation is 11.5 milliliters. The catalyst composition is determined by XRF and XRD and is reported in Tables 2a-2b.

Inventive Example 6

Catalyst $Co_xS_y/Al_2O_3$ is prepared by an incipient wetness impregnation method. The support is basic $Al_2O_3$ doped with 4.5% CaO and 1% MgO (NORPRO SA65169; support properties are reported in Tables 1a-1b). The support is crushed and sieved to 40-80 mesh size. The same catalyst preparation method is used as was used in Inventive Example 1. The mass of support used is 10 grams. The volume of the 2M cobalt (II) thiocyanate solution used for incipient wetness impregnation is 10.68 milliliters. The catalyst composition is determined by XRF and XRD and is reported in Tables 2a-2b.

Inventive Example 7

Catalyst $Co_xS_y/C$ is prepared by an incipient wetness impregnation method. The support is active carbon (Norit GAS 610; support properties are reported in Tables 1a-1b). The support is crushed and sieved to 40-80 mesh size. The same catalyst preparation method is used as was used in Inventive Example 1. The mass of support used is 10 grams. The volume of the 2M cobalt (II) thiocyanate solution used for incipient wetness impregnation is 12 milliliters. The catalyst composition is determined by XRF and XRD and is reported in Tables 2a-2b.

Inventive Example 8

Catalyst $Co_xS_y/C$ is prepared by an incipient wetness impregnation method. The support is active carbon (Sicat Catalyst Meso-C; support properties are reported in Tables 1a-1b). The support is crushed and sieved to 40-80 mesh size. The same catalyst preparation method is used as was used in Inventive Example 1. The mass of support used is 10 grams. The volume of the 2M cobalt (II) thiocyanate solution used for incipient wetness impregnation is 5.2 milliliters. The catalyst composition is determined by XRF and XRD and is reported in Tables 2a-2b.

Inventive Example 9

Catalyst $Co_xS_y/SiO_2$ is prepared by an incipient wetness impregnation method. The support is $SiO_2$ (NORPRO SS61138; support properties are reported in Tables 1a-1b). The support is crushed and sieved to 40-80 mesh size. The same catalyst preparation method is used as was used in Inventive Example 1. The mass of support used is 5 grams. The volume of the 2M cobalt (II) thiocyanate solution used for incipient wetness impregnation is 6.1 milliliters. The catalyst composition is determined by XRF and XRD and is reported in Tables 2a-2b.

Inventive Example 10

Catalyst $Co_xS_y/SiO_2$ is prepared by incipient wetness impregnation method. The support is $SiO_2$ (Fuji Sliysia Cariact Q20C; support properties are reported in Tables 1a-1b). The support is crushed and sieved to 40-80 mesh size. The same catalyst preparation method is used as was used in Inventive Example 1. The mass of support used is 5 grams. The volume of the 2M cobalt (II) thiocyanate solution used for incipient wetness impregnation is 5.1 milliliters. The catalyst composition is determined by XRF and XRD and is reported in Tables 2a-2b.

Inventive Example 11

Catalyst $Co_xS_y/SiO_2$ is prepared by an incipient wetness impregnation method. The support is $SiO_2$ (Fuji Sliysia Cariact Q30C; support properties are reported in Tables 1a-1b). The support is crushed and sieved to 40-80 mesh size. The same catalyst preparation method is used as was used in Inventive Example 1. The mass of support used is 5 grams. The volume of the 2M cobalt (II) thiocyanate solution used for incipient wetness impregnation is 6.1 milliliters. The catalyst composition is determined by XRF and XRD and is reported in Tables 2a-2b.

Inventive Example 12

Catalyst $Co_xS_y/SiO_2$ is prepared by an incipient wetness impregnation method. The support is $SiO_2$ (Fuji Sliysia Cariact Q40C; support properties are reported in Tables 1a-1b). The support is crushed and sieved to 40-80 mesh size. The same catalyst preparation method is used as was used in Inventive Example 1. The mass of support used is 5 grams. The volume of the 2M cobalt (II) thiocyanate solution used for incipient wetness impregnation is 5.1 milliliters. The catalyst composition is determined by XRF and XRD and is reported in Tables 2a-2b.

Inventive Example 13

Catalyst $Co_xS_y/SiO_2$ is prepared by an incipient wetness impregnation method. The support is $SiO_2$ (Fuji Sliysia Cariact Q10; support properties are reported in Tables 1a-1b). The support is crushed and sieved to 40-80 mesh size. The same catalyst preparation method is used as was used in Inventive Example 1. The mass of support used is 10.2 grams. The volume of the 2M cobalt (II) thiocyanate solution used for incipient wetness impregnation is 10.2 milliliters. The drying and autoreduction are carried out as in Example 1 but the final calcination temperature is 400° C. (for 4 hours) instead of 550° C. The catalyst passivation is carried out the same as in Example 1. The catalyst composition is determined by XRF and XRD and is reported in Tables 2a-2b.

Inventive Example 14

Catalyst $Co_xS_y/SiO_2$ is prepared by an incipient wetness impregnation method. The support is $SiO_2$ (Fuji Sliysia Cariact Q20C; support properties are reported in Tables 1a-1b). The support is crushed and sieved to 40-80 mesh size. The same catalyst preparation method is used as was used in Inventive Example 1. The mass of support used is 10.2 grams. The volume of the 2M cobalt (II) thiocyanate solution used for incipient wetness impregnation is 8.0 milliliters. The drying and autoreduction are carried out as in Example 1 but the final calcination temperature is 400° C. (for 4 hours) instead of 550° C. The catalyst passivation is carried out the same as in Example 1. The catalyst composition is determined by XRF and XRD and is reported in Tables 2a-2b.

Inventive Example 15

Catalyst $Co_xS_y/Al_2O_3$ is prepared by an incipient wetness impregnation method. The support is $Al_2O_3$(NORPRO CA 08408; support properties are reported in Tables 1a-1b). The support is crushed and sieved to 40-80 mesh size. The same catalyst preparation method is used as was used in Inventive Example 1. The mass of support used is 11.8 grams. The volume of the 2M cobalt (II) thiocyanate solution used for incipient wetness impregnation is 10 milliliters. The drying and autoreduction are carried out as in Example 1 but the final calcination temperature is 400° C. (for 4 hours) instead of 550° C. The catalyst passivation is carried out the same as in Example 1. The catalyst composition is determined by XRF and XRD and is reported in Tables 2a-2b.

Inventive Example 16

Catalyst $Co_xS_y/SiC$ is prepared by an incipient wetness impregnation method. The support is SiC (from SiCat Catalyst; support properties are reported in Tables 1a-1b). The support is crushed and sieved to 40-80 mesh size. The same catalyst preparation method is used as was used in Inventive Example 1. The mass of support used is 10.6 grams. The volume of the 2M cobalt (II) thiocyanate solution used for incipient wetness impregnation is 5 milliliters. The drying and autoreduction are carried out as in Example 1 but the final calcination temperature is 400° C. (for 4 hours) instead of 550° C. The catalyst passivation is carried out the same as in Example 1. The catalyst composition is determined by XRF and XRD and is reported in Tables 2a-2b.

Inventive Example 17

Catalyst $Co_xS_y/ZrO_2$ is prepared by an incipient wetness impregnation method. The support is $ZrO_2$ (NORPRO SZ31164; support properties are reported in Tables 1a-1b). The support is crushed and sieved to 40-80 mesh size. The same catalyst preparation method is used as was used in Inventive Example 1. The mass of support used is 11.3 grams. The volume of the 2M cobalt (II) thiocyanate solution used for incipient wetness impregnation is 4 milliliters. The drying and autoreduction are carried out as in Example 1 but the final calcination temperature is 400° C. (for 4 hours) instead of 550° C. The catalyst passivation is carried out the same as in Example 1. The catalyst composition is determined by XRF and XRD and is reported in Tables 2a-2b.

Inventive Example 18

Catalyst $Co_xS_y/C$ is prepared by an incipient wetness impregnation method. The support is active carbon (Sicat Catalyst Meso-C; support properties are reported in Tables 1a-1b). The support is crushed and sieved to 40-80 mesh size. The same catalyst preparation method is used as was used in Inventive Example 1. The mass of support used is 10.22 grams. The volume of the 2M cobalt (II) thiocyanate solution used for incipient wetness impregnation is 5 milliliters. The drying and autoreduction are carried out as in Example 1 but the final calcination temperature is 400° C. (for 4 hours) instead of 550° C. The catalyst passivation is carried out the same as in Example 1. The catalyst composition is determined by XRF and XRD and is reported in Tables 2a-2b.

Inventive Example 19

Catalyst $Co_xS_y/TiO_2$ is prepared by an incipient wetness impregnation method. The support is $TiO_2$ (NORPRO ST31119; support properties are reported in Tables 1a-1b). The support is crushed and sieved to 40-80 mesh size. The same catalyst preparation method is used as was used in Inventive Example 1. The mass of support used is 11.22 grams. The volume of the 2M cobalt (II) thiocyanate solution used for incipient wetness impregnation is 5 milliliters. The drying and autoreduction are carried out as in Example 1 but the final calcination temperature is 400° C. (for 4 hours) instead of 550° C. The catalyst passivation is carried out the same as in Example 1. The catalyst composition is determined by XRF and XRD and is reported in Tables 2a-2b.

Comparative Example 1 (Bulk Cobalt Sulfide Catalyst)

Bulk Cobalt sulfide catalyst with $Co_9S_8$ as the dominant crystalline phase is prepared by a co-precipitation method using an aqueous solution of cobalt (II) acetate tetrahydrate (440 g $Co(CH_3COO)_2 \cdot 4H_2O$, purchased from Sigma Aldrich) in 3200 ml $H_2O$ with an aqueous solution of ammonium sulfide (531.7 g $(NH_4)_2S$, 20%, purchased from Sigma Aldrich) at 60° C.

After precipitation, the samples are left at 60° C. for 15 minutes to age and then cooled down to room temperature. The final pH for the slurry is ~6.9. The resulting precipitate is washed 3 times with deionized water (500 milliliters each wash) and centrifuged for 15 minutes at 6000 rpm. The samples are then dried in a vacuum oven at 60° C. overnight (18 hours) and are thermally treated at 550° C. under 50 milliliters/minute $N_2$ flow for 1 hour in a tube furnace followed by room temperature passivation with 1% $O_2$/Ar for 2 hours. The BET surface area of this sample measured by $N_2$ ads/des is 10.7 $m^2/g$. The catalyst contains $Co_{1-x}S$ and $Co_9S_8$ phases according to XRD. The catalyst is tabletized, crushed, and sieved to 40-80 mesh size prior to testing. The catalyst composition is determined by XRF and XRD and is reported in Tables 2a-2b.

Comparative Example 2

Catalyst $Co_xS_y/Al_2O_2$ is prepared by an incipient wetness impregnation method. The support is $Al_2O_3$(NORPRO SA51161; support properties are reported in Tables 1a-1b). The support is crushed and sieved to 40-80 mesh size. The same catalyst preparation method is used as was used in Inventive Example 1. The mass of support used is 9.2 grams. The volume of the 2M cobalt (II) thiocyanate solution used for incipient wetness impregnation is 4.692 milliliters. The catalyst composition is determined by XRF and XRD and is reported in Tables 2a-2b.

Comparative Example 3

Catalyst $Co_xS_y/Al_2O_3$ is prepared by incipient wetness impregnation method.

Preparation of $CoO/Al_2O_3$

First, an impregnation solution of cobalt (II) acetate in deionized water is prepared at a concentration of 1 molar (M). Then, 5 grams of 40-80 mesh size $Al_2O_3$ support (NORPRO SA31132; support properties are reported in Tables 1a-1b) are placed in a porcelain dish and 5 ml of the impregnation solution is added dropwise while gently shaking. The as impregnated catalyst is dried in the box oven on air for 2 hours at 120° C. The impregnation is repeated two more times with drying on air after each impregnation. In total, three impregnations are made. Total volume of the 1M cobalt (II) acetate solution used for the three incipient wetness impregnations: 15.0 ml. The impregnated catalyst is dried and calcined on air using the following program: temperature is increased from room temperature to 120° C. at 2° C./min, dwell at 120° C. for 2 hours, increase from 120 to 400° C. at 3° C./min, dwell at 400° C. for 4 hours, cool down to room temperature resulting in supported cobalt oxide material $CoO_x/Al_2O_3$.

Sulfidation of $CoO/Al_2O_3$

The as-prepared $CoO_x/Al_2O_3$ is sulfided in the liquid phase using aqueous ammonium sulfide solution. For this purpose, 25 milliliters of deionized water and 25 milliliters of 20 wt % aqueous ammonium sulfide are added to a 250 milliliter glass beaker, equipped with a magnetic stirbar and a thermocouple. The solution is heated to 60° C. and then 5 grams of the $CoO_x/Al_2O_3$ material are added to the solution and the slurry is stirred for 20 minutes at 60° C. (±5° C.). The cake is recovered by filtration through the filter paper and washed with 500 ml of deionized water.

The cake is dried overnight on air at room temperature. Then, the dried cake is placed in the stainless steel drum for drying, autoreduction and passivation. The drying and autoreduction are carried out in the flow of pure $N_2$ (overhead flow 5.5 liters/min) using the following program: flush with $N_2$ flow for 30 minutes at room temperature, increase temperature from room temperature to 120° C. at 2° C./minute, dwell at 120° C. for 2 hours, increase from 120 to 550° C. at 3° C./minute, dwell at 550° C. for 4 hours, cool down to room temperature 20-25° C. (24-48 hours). After that, the catalyst is passivated in 1 vol %02/$N_2$ flow for 2 hours at room temperature (20-25° C.). The oxygen concentration in the gas flow is then gradually increased to 21 vol % $O_2/N_2$. The catalyst is purged for 1 hour in 21 vol % $O_2/N_2$ prior to opening the stainless steel drum. The result is black color supported cobalt sulfide catalyst. The catalyst composition is determined by XRF and XRD and is reported in Tables 2a-2b.

Comparative Example 4

Catalyst $Co_xS_y/Al_2O_3$ is prepared using preparation method described in Comparative Example 3.

Preparation of $CoO_x/Al_2O_3$

The same preparation method as described in Comparative Example 3 is used for this Comparative Example. The support is $Al_2O_3$(NORPRO SA6176; support properties are reported in Tables 1a-1b). The support is crushed and sieved to 40-80 mesh size. The mass of support used is 5 grams. The total volume of the 1M cobalt (II) acetate solution used for the three incipient wetness impregnations is 17.25 milliliters.

Sulfidation of $CoO_x/Al_2O_3$

The same sulfidation method as described in Comparative Example 3 is used for this Comparative Example.

The catalyst composition is determined by XRF and XRD and is reported in Tables 2a-2b.

Comparative Example 5

Catalyst $Co_xS_y/Al_2O_3$ is prepared using the preparation method described in Comparative Example 3.

Preparation of $CoO_x/Al_2O_3$

The same preparation method as described in Comparative Example 3 is used for this Comparative Example. The support is $Al_2O_3$ (NORPRO SA6178; support properties are reported in Tables 1a-1b). The support is crushed and sieved to 40-80 mesh size. The mass of support used is 5 grams. The total volume of the 1M cobalt (II) acetate solution used for the three incipient wetness impregnations is 13.05 milliliters.

Sulfidation of $CoO_x/Al_2O_3$

The same sulfidation method as described in Comparative Example 3 is used for this Comparative Example.

The catalyst composition is determined by XRF and XRD and is reported in Tables 2a-2b.

Comparative Example 6

Catalyst $Co_xS_y/SiO_2$ is prepared using the preparation method described in Comparative Example 3.

Preparation of $CoO_x/Si_2O_2$

The same preparation method as described in Comparative Example 3 is used for this Comparative Example. The support is $SiO_2$ (NORPRO SS61138; support properties are reported in Tables 1a-1b). The support is crushed and sieved to 40-80 mesh size. The mass of support used is 5 grams. The total volume of the 1M cobalt (II) acetate solution used for the three incipient wetness impregnations is 18 milliliters.

Sulfidation of $CoO_x/SiO_2$

The same sulfidation method as described in Comparative Example 3 is used for this Comparative Example.

The catalyst composition is determined by XRF and XRD and is reported in Tables 2a-2b.

Comparative Example 7

Catalyst $Co_xS_y/SiO_2$ is prepared using the preparation method described in Comparative Example 3.

Preparation of $CoO_x/Si_2O_2$

The same preparation method as described in Comparative Example 3 is used for this Comparative Example. The support is $SiO_2$ (Fuji Sliysia Cariact Q10; support properties are reported in Tables 1a-1b). The support is crushed and sieved to 40-80 mesh size. The mass of support used is 5 grams. The total volume of the 1M cobalt (II) acetate solution used for the three incipient wetness impregnations is 12.9 milliliters.

Sulfidation of $CoO_x/SiO_2$

The same sulfidation method as described in Comparative Example 3 is used for this Comparative Example.

The catalyst composition is determined by XRF and XRD and is reported in Tables 2a-2b.

Comparative Example 8

Catalyst $Co_xS_y/SiO_2$ is prepared using the preparation method described in Comparative Example 3.

Preparation of $CoO_x/Si_2O_2$

The same preparation method as described in Comparative Example 3 is used for this Comparative Example. The support is $SiO_2$ (Fuji Sliysia Cariact Q20C; support properties are reported in Tables 1a-1b). The support is crushed and sieved to 40-80 mesh size. The mass of support used is 5 grams. The total volume of the 1M cobalt (II) acetate solution used for the three incipient wetness impregnations is 15 milliliters.

Sulfidation of $CoO_x/SiO_2$

The same sulfidation method as described in Comparative Example 3 is used for this Comparative Example.

The catalyst composition is determined by XRF and XRD and is reported in Tables 2a-2b.

Comparative Example 9

Supported cobalt oxide catalyst $CoO_x/Al_2O_3$ is prepared using the preparation method described in Comparative Example 3.

The support is $Al_2O_3$(NORPRO SA31132; support properties are reported in Tables 1a-1b). The support is crushed and sieved to 40-80 mesh size. The mass of support used is 10 grams. The total volume of the 1M cobalt (II) acetate solution used for the three incipient wetness impregnations is 20 milliliters.

The catalyst composition determined by XRF and XRD is reported in Tables 2a-2b.

Comparative Example 10

Supported cobalt oxide catalyst $CoO_x/Al_2O_3$ is prepared using the preparation method described in Comparative Example 3.

The support is $Al_2O_3$(NORPRO SA6176; support properties are reported in Tables 1a-1b). The support is crushed and sieved to 40-80 mesh size. The mass of support used is 10 grams. The total volume of the 1M cobalt (II) acetate solution used for two incipient wetness impregnations is 23 milliliters.

The catalyst composition determined by XRF and XRD is reported in Tables 2a-2b.

Comparative Example 11

Supported cobalt oxide catalyst $CoO_x/Al_2O_3$ is prepared using the preparation method described in Comparative Example 3.

The support is $Al_2O_3$ (NORPRO SA6178; support properties are reported in Tables 1a-1b). The support is crushed and sieved to 40-80 mesh size. The mass of support used is 10 grams. The total volume of the 1M cobalt (II) acetate solution used for two incipient wetness impregnations is 17.4 milliliters.

The catalyst composition determined by XRF and XRD is reported in Tables 2a-2b.

Comparative Example 12

Supported cobalt oxide catalyst $CoO_x/Al_2O_3$ is prepared using the preparation method described in Comparative Example 3.

The support is $Al_2O_3$—$SiO_2$ (SASOL Siralox 1.5/140 in the powder form; support properties are reported in Tables 1a-1b). The mass of support used is 10 grams. The total volume of the 1M cobalt (II) acetate solution used for two incipient wetness impregnations is 19 milliliters. After preparation the catalyst is pelletized, crushed and sieved to 40-80 mesh size.

The catalyst composition is determined by XRF and XRD and is reported in Tables 2a-2b.

Comparative Example 13

Supported cobalt oxide catalyst $CoO_x/SiO_2$ is prepared using the preparation method described in Comparative Example 3.

The support is $SiO_2$ (NORPRO SS61138; support properties are reported in Tables 1a-1b). The support is crushed and sieved to 40-80 mesh size. The mass of the support used is 10 grams. The total volume of the 1M cobalt (II) acetate solution used for two incipient wetness impregnations is 24 milliliters.

The catalyst composition is determined by XRF and XRD and is reported in Tables 2a-2b.

TABLE 1a

Properties of Supports Used for Catalyst Preparation

| | | Support material | Support ID | Phase | BET Surface area [m$^2$/g] |
|---|---|---|---|---|---|
| Inventive Ex. 1 | Comparative Exs. 3 & 9 | $Al_2O_3$ | NORPRO SA31132 | theta | 55 |
| Inventive Ex. 2 | | $Al_2O_3$ | NORPRO SA6173 | gamma | 200 |
| Inventive Ex. 3 | Comparative Exs. 5 & 11 | $Al_2O_3$ | NORPRO SA6178 | gamma/delta | 175 |
| Inventive Ex. 4 | Comparative Ex. 12 | $Al_2O_3$—$SiO_2$ | SASOL Siralox 1.5/140 | n.a. | 146 |
| Inventive Ex. 5 | Comparative Exs. 4 & 10 | $Al_2O_3$ | NORPRO SA6176 | gamma | 250 |
| Inventive Ex. 6 | | $Al_2O_3$ | NORPRO SA65169 | n.a. | 250 |
| Inventive Ex. 7 | | Carbon | Norit GAS 610 | n.a. | n.m |
| Inventive Exs. 8 & 18 | | Carbon | SiCat Catalyst Meso-C | n.a. | 285 |
| Inventive Ex. 9 | Comparative Exs. 6 & 13 | $SiO_2$ | NORPRO SS61138 | n.a. | 250 |
| Inventive Exs. 10 & 14 | Comparative Ex. 8 | $SiO_2$ | Fuji Sliysia Cariact Q20C | n.a. | 140 |
| Inventive Ex. 11 | | $SiO_2$ | Fuji Sliysia Cariact Q30C | n.a. | 95 |
| Inventive Ex. 12 | | $SiO_2$ | Fuji Sliysia Cariact Q40C | n.a. | 70 |
| | Comparative Ex. 2 | $Al_2O_3$ | NORPRO SA51161 | alpha | 4.5 |
| Inventive Ex. 16 | | SiC | SiCat Catalyst SiC | beta | 29 |
| Inventive Ex. 13 | Comparative Ex. 7 | $SiO_2$ | Fuji Sliysia Cariact Q10 | n.a. | 300 |
| Inventive Ex. 15 | | $Al_2O_3$ | NORPRO CA 08408 | gamma | 245 |
| Inventive Ex. 17 | | $ZrO_2$ | NORPRO SZ31164 | monoclinic | 100 |

*BJH adsorption average pore width (4V/A)
n.a.—not available

TABLE 1b

Properties of Supports Used for Catalyst Preparation

| | | Support material | Support ID | Pore diameter [nm]** | Incipient wetness pore volume determined by DI water [cm$^3$/g]** |
|---|---|---|---|---|---|
| Inventive Ex. 1 | Compar. Exs. 3 & 9 | $Al_2O_3$ | NORPRO SA31132 | 25/550 (median) | 1.00 |
| Inventive Ex. 2 | | $Al_2O_3$ | NORPRO SA6173 | 7 (median) | 0.90 |
| Inventive Ex. 3 | Compar. Exs. 5 & 11 | $Al_2O_3$ | NORPRO SA6178 | 13 (median) | 0.87 |
| Inventive Ex. 4 | Compar. Ex. 12 | $Al_2O_3$—$SiO_2$ | SASOL Siralox 1.5/140 | 12 (average)* | 0.95 |
| Inventive Ex. 5 | Compar. Ex. 4 & 10 | $Al_2O_3$ | NORPRO SA6176 | 7/500 (median) | 1.15 |
| Inventive Ex. 6 | | $Al_2O_3$ | NORPRO SA65169 | 10 and 110 (bimodal) | 1.07 |

TABLE 1b-continued

| Properties of Supports Used for Catalyst Preparation | | | | | |
|---|---|---|---|---|---|
| | | Support material | Support ID | Pore diameter [nm]** | Incipient wetness pore volume determined by DI water [$cm^3/g$]** |
| Inventive Ex. 7 | | Carbon | Norit GAS 610 | n.m. | 1.20 |
| Inventive Exs. 8 & 18 | | Carbon | SiCat Catalyst Meso-C | 13 (average)* | 0.52 |
| Inventive Ex. 9 | Compar. Exs. 6 & 13 | $SiO_2$ | NORPRO SS61138 | 12 | 1.20 |
| Inventive Exs. 10 & 14 | Compar. Ex. 8 | $SiO_2$ | Fuji Sliysia Cariact Q20C | 20 | 1.00 |
| Inventive Ex. 11 | | $SiO_2$ | Fuji Sliysia Cariact Q30C | 30 | 1.22 |
| Inventive Ex. 12 | | $SiO_2$ | Fuji Sliysia Cariact Q40C | 40 | 1.00 |
| | Compar. Ex. 2 | $Al_2O_3$ | NORPRO SA51161 | 100/1100 | 0.51 |
| Inventive Ex. 16 | | SiC | SiCat Catalyst SiC | 20 (average)* | 0.95 |
| Inventive Ex. 13 | Compar. Ex. 7 | $SiO_2$ | Fuji Sliysia Cariact Q10 | 10 | 0.86 |
| Inventive Ex. 15 | | $Al_2O_3$ | NORPRO CA 08408 | 9.4 | 0.89 |
| Inventive Ex. 17 | | $ZrO_2$ | NORPRO SZ31164 | 12 | 0.4 |

*BJH adsorption average pore width (4V/A)

**from supplier n.m.—not measured

TABLE 2a

Composition of Catalysts in Inventive Examples 1-19 and Comparative Examples 1-13 Unless stated otherwise, for each of the Inventive and Comparative Examples in Table 2, the remaining weight percentage of the composition is oxygen.

| | Support material | Co Wt Percent | S Wt Percent | Al Wt Percent | Si Wt Percent | Cl Wt Percent | Ca Wt Percent |
|---|---|---|---|---|---|---|---|
| Inventive Ex. 1 | $Al_2O_3$ | 8.91 | 4.25 | 44.09 | 0.044 | | |
| Inventive Ex. 2 | $Al_2O_3$ | 10.12 | 6.46 | 42.02 | 0.033 | 0.024 | |
| Inventive Ex. 3 | $Al_2O_3$ | 10.33 | 5.66 | 42.33 | 0.036 | | |
| Inventive Ex. 4 | $Al_2O_3$ | 9.55 | 4.36 | 43.0 | 0.567 | | |
| Inventive Ex. 5 | $Al_2O_3$ | 12.51 | 7.61 | 39.64 | 0.072 | | |
| Inventive Ex. 6 | $Al_2O_3$ | 13.63 | 8.58 | 35.53 | 0.169 | 0.022 | 3.22 |
| Inventive Ex. 7 | Carbon* | 11.86** | 5.59* | 0.69 | 0.83 | | 0.892 |
| Inventive Ex. 8 | Carbon* | 5.66** | 2.28* | | 0.16 | | |
| Inventive Ex. 9 | $SiO_2$ | 11.92 | 6.29 | 0.143 | 35.96 | | 0.047 |
| Inventive Ex. 10 | $SiO_2$ | 9.77 | 5.88 | 0.015 | 37.64 | | 0.048 |
| Inventive Ex. 11 | $SiO_2$ | 10.22 | 4.56 | | 37.95 | | 0.066 |
| Inventive Ex. 12 | $SiO_2$ | 9.12 | 4.74 | | 38.6 | | 0.062 |
| Inventive Ex. 13 | $SiO_2$ | 9.1 | 8.25 | | 36.47 | | 0.017 |
| Inventive Ex. 14 | $SiO_2$ | 8.37 | 6.25 | | 38.37 | | 0.045 |
| Inventive Ex. 15 | $Al_2O_3$ | 8.58 | 7.25 | 42.67 | 0.081 | 0.023 | |
| Inventive Ex. 16 | SiC | 2.76 | 2.05 | | 43.93 | | |
| Inventive Ex. 17 | $ZrO_2$ | 3.67 | 2.54 | | 0.039 | | |
| Inventive Ex. 18 | Carbon* | 11.6 | 5.4 | | | | |
| Inventive Ex. 19 | $TiO_2$ | 4.82 | 3.38 | | 0.032 | | 0.017 |
| Compar. Ex. 1^ | Bulk | 63.9 | 36.1 | | | | |
| Compar. Ex. 2 | $Al_2O_3$ | 5.36 | 1.99 | 47.45 | 0.312 | | 0.042 |
| Compar. Ex. 3 | $Al_2O_3$ | 14.88 | 7.00 | 38.34 | 0.05 | | |
| Compar. Ex. 4 | $Al_2O_3$ | 21.94 | 7.53 | 32.93 | 0.08 | | |
| Compar. Ex. 5 | $Al_2O_3$ | 12.89 | 5.98 | 40.32 | 0.04 | | |
| Compar. Ex. 6 | $SiO_2$ | 18.06 | 5.58 | 0.19 | 32.33 | | 0.04 |
| Compar. Ex. 7 | $SiO_2$ | 15.30 | 8.24 | 0.08 | 32.95 | | 0.06 |
| Compar. Ex. 8 | $SiO_2$ | 17.00 | 10.93 | 0.03 | 30.65 | | 0.04 |
| Compar. Ex. 9 | $Al_2O_3$ | 7.83 | | 47.16 | 0.0432 | | |
| Compar. Ex. 10 | $Al_2O_3$ | 12.7 | | 43.63 | 0.0521 | 0.02 | |
| Compar. Ex. 11 | $Al_2O_3$ | 11.43 | | 44.58 | 0.0293 | | |

TABLE 2a-continued

Composition of Catalysts in Inventive Examples 1-19 and Comparative Examples 1-13 Unless stated otherwise, for each of the Inventive and Comparative Examples in Table 2, the remaining weight percentage of the composition is oxygen.

| | Support material | Co Wt Percent | S Wt Percent | Al Wt Percent | Si Wt Percent | Cl Wt Percent | Ca Wt Percent |
|---|---|---|---|---|---|---|---|
| Compar. Ex. 12 | $SiO_2$ | 8.27 | | 46.2 | 0.629 | | |
| Compar. Ex. 13 | $Al_2O_3$ | 10.94 | | 0.104 | 39.58 | | 0.049 |

*Balance - carbon

**Calculated from the impregnated cobalt amount and S/Co ratio determined by XRF

***Two phases of cobalt sulfide were detected by XRD: $Co_{1-x}S$ and $Co_9S_8$ in ~1:1 wt/wt ratio ^Sample composition derived from XRD.

TABLE 2b

Composition of Catalysts in Inventive Examples 1-19 and Comparative Examples 1-13

| | Support material | Ti Wt Percent | Other Wt Percent | S/Co ratio (mol/mol) | Particle size $Co_{1-x}S$ (102) 46.727 2-theta [nm] | Particle size $Co_9S_8$ (440) 51.965 2-theta [nm] |
|---|---|---|---|---|---|---|
| Inventive Ex. 1 | $Al_2O_3$ | | | 0.88 | 8 | — |
| Inventive Ex. 2 | $Al_2O_3$ | 0.025 | | 1.18 | 3 | — |
| Inventive Ex. 3 | $Al_2O_3$ | | | 1.01 | 3 | — |
| Inventive Ex. 4 | $Al_2O_3$ | | | 0.84 | 7 | — |
| Inventive Ex. 5 | $Al_2O_3$ | 0.016 | | 1.12 | 3 | — |
| Inventive Ex. 6 | $Al_2O_3$ | | | 1.16 | 4 | — |
| Inventive Ex. 7 | Carbon* | 0.201 | | 0.87 | 26*** | 16 |
| Inventive Ex. 8 | Carbon* | | | 0.74 | 21*** | 14 |
| Inventive Ex. 9 | $SiO_2$ | | | 0.97 | 12 | — |
| Inventive Ex. 10 | $SiO_2$ | | | 1.11 | 9 | — |
| Inventive Ex. 11 | $SiO_2$ | 0.016 | | 0.82 | 12 | — |
| Inventive Ex. 12 | $SiO_2$ | | | 0.96 | 10 | — |
| Inventive Ex. 13 | $SiO_2$ | | | 1.53 | — | — |
| Inventive Ex. 14 | $SiO_2$ | | | 1.38 | — | — |
| Inventive Ex. 15 | $Al_2O_3$ | 0.029 | | 1.56 | — | — |
| Inventive Ex. 16 | SiC | 0.074 | | 1.37 | — | — |
| Inventive Ex. 17 | $ZrO_2$ | | 66.27 wt. % $ZrO_2$ 2.36 wt. % Hf | 1.27 | — | — |
| Inventive Ex. 18 | Carbon* | | | 0.86 | — | — |
| Inventive Ex. 19 | $TiO_2$ | 53.48 | 0.023 wt. % $P_x$ | 1.29 | — | — |
| Compar. Ex. 1^ | Bulk | | | 1.04 | | |
| Compar. Ex. 2 | $Al_2O_3$ | 0.017 | | 0.68 | 30 | — |
| Compar. Ex. 3 | $Al_2O_3$ | | | 0.87 | 16 | — |
| Compar. Ex. 4 | $Al_2O_3$ | | | 0.63 | — | — |
| Compar. Ex. 5 | $Al_2O_3$ | | | 0.85 | 18 | — |
| Compar. Ex. 6 | $SiO_2$ | | | 0.57 | — | — |
| Compar. Ex. 7 | $SiO_2$ | | | 0.99 | — | — |
| Compar. Ex. 8 | $SiO_2$ | | | 1.18 | 13 | — |
| Compar. Ex. 9 | $Al_2O_3$ | | | — | — | — |
| Compar. Ex. 10 | $Al_2O_3$ | | | — | — | — |
| Compar. Ex. 11 | $Al_2O_3$ | | | — | — | — |
| Compar. Ex. 12 | $SiO_2$ | | | — | — | — |
| Compar. Ex. 13 | $Al_2O_3$ | | | — | — | — |

*Balance - carbon

**Calculated from the impregnated cobalt amount and S/Co ratio determined by XRF

***Two phases of cobalt sulfide were detected by XRD: $Co_{1-x}S$ and $Co_9S_8$ in ~1:1 wt/wt ratio ^Sample composition derived from XRD.

Catalytic Tests of Inventive Examples 1-19 and Comparative Examples 1-13

Kinetic Measurements

The kinetic measurements of cobalt sulfide catalysts are evaluated using fixed bed reactors under the conditions specified in Table 3. The reactor is loaded with 1 gram of the sized catalyst (40-80 mesh) with the catalyst bed sandwiched between layers of 20-40 mesh quartz chips. The reactors are leak-tested at 750 psig under $N_2$ and then started up by flowing under dry reactant gas feed containing 8% ethylene, 56% CO and 16% $N_2$ with a flow rate of 50 standard cubic centimeters per minute (sccm). A liquid water feed is introduced at >150° C. at a rate of 2.5 milligram/minute, which leads to a feed composition as ethylene/CO/water/$N_2$ (vol %)=~7.5%/~53.5%/~5.9%/bal in the total gas stream. For Conditions 1 and 2 in Table 3, when the reaction temperature reached 270° C., it is considered as the beginning of the reaction. The catalysts are first tested at 270° C. for several hours (Condition 1) and then at 290° C. (Condition 2). For Conditions 3-5 in Table 3, when the reaction temperature reached 250° C., it is considered as the beginning of the reaction. The catalysts are first tested at 250° C. for several hours (Condition 3), then at 270° C. for several hours (Condition 4), and then at 290° C. for several hours (Condition 5).

X-ray Fluorescence (XRF) Measurements

X-ray Fluorescence (XRF) data are collected at room temperature (RT) with a PANalytical PW4400 spectrometer using an X-ray tube with a rhodium anode.

Powder X-Ray Diffraction (XRD)

The P-XRD measurement is carried out at ambient lab conditions on a Bruker AXS diffractometer D8 Discover with General Area Diffraction Detector System (GADDS) using Cu Kα (λ=1.5406 Å). 2-theta ranges from 9-70° with a 0.05° integration step size are recorded. The XRD patterns, after 2-theta calibration against a reference standard ($Al_2O_3$ corundum, PDF #00-046-1212).

The references used for cobalt sulfide phases are:

$Co_{1-x}S$ ("$Co_7S_8$")—PDF #00-042-0826, 04-022-8171

$Co_9S_8$—PDF #01-073-6395, 04-004-4525

CoS—PDF #01-075-0605, 03-065-3418

$CoS_2$—PDF #04-004-6455

$Co_4S_3$—PDF #00-030-0458 (cubic), 00-002-1458 (hexagonal)

$Co_3S_4$—PDF #04-006-5317

$Co_3O_4$—PDF #00-042-1467

CoO—PDF #01-076-3832

The results are shown in Tables 4-6.

Inventive Examples 1-19 demonstrate that supported cobalt sulfide catalysts can be prepared by incipient wetness impregnation followed by thermal decomposition of cobalt (II) thiocyanate under inert conditions. When used in some embodiments of gas phase processes of the present invention, the as-prepared catalysts show high selectivity to propionic acid. The preparation method is versatile and enables preparation of catalysts across different classes of supports: alumina, silica, carbon and others.

Comparative Example 1 is a bulk cobalt sulfide catalyst. Comparison of the Inventive Examples with Comparative Example 1 demonstrates that comparable activity and selectivity performance of supported catalysts can be achieved at lower cobalt loadings in the supported catalysts (<15 wt % Co) according to some embodiments of the present invention relative to the bulk catalyst (67.4 wt % Co).

Comparative Example 2 demonstrates that not all supports are suitable for the preparation of cobalt sulfide catalysts in accordance with some embodiments of the present invention. Comparative Example 2 show that oxide supports with low surface area (<5 $m^2/g$) such as alpha alumina yield catalysts with low activity, presumably due to formation of large cobalt sulfide crystallites.

Comparative Examples 3-8 show that supported cobalt sulfide catalysts prepared by sulfidation of cobalt oxide and autoreduced at 550° C. have lower activity compared to the catalysts prepared in accordance with some embodiments of the present invention.

Comparative Examples 9-13 show that other classes of catalysts (i.e., supported cobalt oxides) are not active in the direct synthesis of propionic acid.

Calculations of Catalyst Performance for Inventive Examples and Comparative Examples The carbon balance is defined and calculated as follows:

$$\text{Mass balance} = \frac{\sum (n_i \times V_i)_{outlet}}{\sum (n_i \times V_i)_{inlet}}$$

here $n_i$ is the number of carbons in species $V_i$, and Vi represents the molar flow rates of species i.

$$\text{ethylene conversion} = \frac{\left(\sum \sigma i \times Cpi\right)_{out}}{\left(\sum (\sigma i \times Cpi + \sigma i \times Cri)\right)_{out}}$$

where Cpi is concentration of all the products with carbon number ≥2 and Cri is the reactants at the reactor outlet.

$$PA \text{ slectivity } (C2 \text{ basis, } \%) = \frac{CpA}{\sum_{n \geq 2} (\sigma_i \times C_{pi})_{outlet}}$$

(Assuming that all the products with carbon number ≥2 are derived from ethylene)

where $\sigma_i$ is the stoichiometry with respect to C2 in which $\sigma_i$=2 for C4s and $\sigma_i$=3 for C6s and $\sigma_i$=1 for all the other products such as aldehydes, alcohols and esters.

TABLE 3

Conditions for Testing Inventive Examples 1-19 and Comparative Examples 1-13

| | Ethylene [vol %] | CO [vol %] | H2O [vol %] | N2 [vol %] | Catalyst load [g] | WHSV* [h−1] | T [° C.] | P [psig] | Time-on-stream [h] |
|---|---|---|---|---|---|---|---|---|---|
| Condition 1 | 7.5 | 53.5 | 5.9 | Balance | 1 | 3.7 | 270 | 750 | 2-20 |
| Condition 2 | 7.5 | 53.5 | 5.9 | Balance | 1 | 3.7 | 290 | 750 | 22-40 |
| Condition 3 | 7.5 | 53.5 | 5.9 | Balance | 1 | 3.7 | 250 | 750 | 2-7 |
| Condition 4 | 7.5 | 53.5 | 5.9 | Balance | 1 | 3.7 | 270 | 750 | 10-25 |
| Condition 5 | 7.5 | 53.5 | 5.9 | Balance | 1 | 3.7 | 290 | 750 | 30-35 |

*weight hourly space velocity

TABLE 4a

Catalytic Data for Inventive Examples 1-12

| | | Ethylene | Selectivity, Cmol % | | | | |
|---|---|---|---|---|---|---|---|
| Example | Condition | Conversion, Cmol % | Propionic acid | Ethane | 1-Propanol | Propionaldehyde | Methyl acetate |
| Inv. Ex. 1 | 1 | 7.7 | 91.6 | 3.9 | 0.3 | 3.0 | 0.0 |
| Inv. Ex. 2 | 1 | 12.0 | 91.2 | 4.1 | 0.2 | 3.1 | 0.0 |
| Inv. Ex. 3 | 1 | 11.6 | 90.3 | 4.9 | 0.3 | 3.2 | 0.0 |

TABLE 4a-continued

Catalytic Data for Inventive Examples 1-12

| Example | Condition | Ethylene Conversion, Cmol % | Selectivity, Cmol % Propionic acid | Ethane | 1-Propanol | Propionaldehyde | Methyl acetate |
|---|---|---|---|---|---|---|---|
| Inv. Ex. 4* | 1 | 15.1 | 94.5 | 2.8 | 0.1 | 1.3 | 0.0 |
| Inv. Ex. 5 | 1 | 11.1 | 88.3 | 5.4 | 0.4 | 4.5 | 0.0 |
| Inv. Ex. 6 | 1 | 14.0 | 85.3 | 6.0 | 0.7 | 5.9 | 0.0 |
| Inv. Ex. 7 | 1 | 11.2 | 84.3 | 12.3 | 0.1 | 1.5 | 0.0 |
| Inv. Ex. 8 | 1 | 10.3 | 88.4 | 7.0 | 0.1 | 1.8 | 0.0 |
| Inv. Ex. 9 | 1 | 22.2 | 95.8 | 2.3 | 0.1 | 1.2 | 0.0 |
| Inv. Ex. 10 | 1 | 19.4 | 97.5 | 1.5 | 0.0 | 0.6 | 0.0 |
| Inv. Ex. 11 | 1 | 10.8 | 96.3 | 1.8 | 0.0 | 1.2 | 0.0 |
| Inv. Ex. 12 | 1 | 10.9 | 95.7 | 2.1 | 0.1 | 1.5 | 0.0 |
| Inv. Ex. 1 | 2 | 8.5 | 87.6 | 7.1 | 0.6 | 3.3 | 0.1 |
| Inv. Ex. 3 | 2 | 12.4 | 85.5 | 8.3 | 0.7 | 3.5 | 0.2 |
| Inv. Ex. 5 | 2 | 14.4 | 83.1 | 10.2 | 0.8 | 4.0 | 0.1 |
| Inv. Ex. 6 | 2 | 19.9 | 84.2 | 8.2 | 1.0 | 4.1 | 0.1 |
| Inv. Ex. 7 | 2 | 9.1 | 77.2 | 19.1 | 0.4 | 1.5 | 0.1 |
| Inv. Ex. 8 | 2 | 10.4 | 87.6 | 8.5 | 0.1 | 1.6 | 0.0 |
| Inv. Ex. 9 | 2 | 28.1 | 93.4 | 4.3 | 0.2 | 1.5 | 0.0 |

*Data is averaged of 2-8 hrs on stream

TABLE 4b

Catalytic Data for Inventive Examples 1-12

| Example | Condition | Selectivity, Cmol % Ethyl acetate | Propyl acetate | 1-Methoxypropanel | 1-Ethoxypropane | Propylene | Propane |
|---|---|---|---|---|---|---|---|
| Inv. Ex. 1 | 1 | 0.0 | 0.8 | 0.0 | 0.2 | 0.0 | 0.0 |
| Inv. Ex. 2 | 1 | 0.0 | 0.7 | 0.0 | 0.5 | 0.0 | 0.0 |
| Inv. Ex. 3 | 1 | 0.0 | 0.6 | 0.0 | 0.5 | 0.0 | 0.0 |
| Inv. Ex. 4* | 1 | 0.0 | 0.2 | 0.5 | 0.5 | 0.0 | 0.0 |
| Inv. Ex. 5 | 1 | 0.0 | 0.9 | 0.0 | 0.5 | 0.0 | 0.0 |
| Inv. Ex. 6 | 1 | 0.0 | 1.3 | 0.1 | 0.7 | 0.1 | 0.0 |
| Inv. Ex. 7 | 1 | 0.0 | 1.3 | 0.3 | 0.2 | 0.0 | 0.0 |
| Inv. Ex. 8 | 1 | 0.0 | 2.5 | 0.1 | 0.1 | 0.0 | 0.0 |
| Inv. Ex. 9 | 1 | 0.0 | 0.4 | 0.0 | 0.2 | 0.0 | 0.0 |
| Inv. Ex. 10 | 1 | 0.0 | 0.2 | 0.0 | 0.2 | 0.0 | 0.0 |
| Inv. Ex. 11 | 1 | 0.0 | 0.5 | 0.0 | 0.1 | 0.0 | 0.0 |
| Inv. Ex. 12 | 1 | 0.0 | 0.5 | 0.0 | 0.1 | 0.0 | 0.0 |
| Inv. Ex. 1 | 2 | 0.1 | 0.8 | 0.0 | 0.4 | 0.0 | 0.0 |
| Inv. Ex. 3 | 2 | 0.1 | 1.0 | 0.0 | 0.6 | 0.1 | 0.0 |
| Inv. Ex. 5 | 2 | 0.0 | 0.9 | 0.0 | 0.9 | 0.2 | 0.0 |
| Inv. Ex. 6 | 2 | 0.0 | 1.4 | 0.0 | 1.0 | 0.1 | 0.0 |
| Inv. Ex. 7 | 2 | 0.0 | 1.4 | 0.1 | 0.2 | 0.0 | 0.0 |
| Inv. Ex. 8 | 2 | 0.1 | 1.8 | 0.1 | 0.1 | 0.0 | 0.0 |
| Inv. Ex. 9 | 2 | 0.0 | 0.3 | 0.0 | 0.2 | 0.0 | 0.0 |

*Data is averaged of 2-8 hrs on stream

TABLE 4c

Catalytic Data for Inventive Examples 1-12

| Example | Condition | Selectivity, Cmol % Propionic acid productivity [g/h/kg_cat] | Carbon dioxide rate [g/h/kg_cat] | Water Gas Shift activity (proxy) [—] | Carbon balance [%] |
|---|---|---|---|---|---|
| Inv. Ex. 1 | 1 | 56.4 | 21.5 | 2.8 | 107.4 |
| Inv. Ex. 2 | 1 | 88.0 | 43.9 | 2.2 | 100.7 |
| Inv. Ex. 3 | 1 | 81.2 | 46.6 | 2.0 | 100.5 |
| Inv. Ex. 4* | 1 | 118.2 | 32.6 | 3.6 | 101.5 |
| Inv. Ex. 5 | 1 | 79.6 | 49.1 | 1.9 | 101.0 |
| Inv. Ex. 6 | 1 | 96.7 | 65.6 | 1.5 | 101.0 |
| Inv. Ex. 7 | 1 | 79.3 | 18.3 | 5.0 | 101.2 |

TABLE 4c-continued

Catalytic Data for Inventive Examples 1-12

| Example | Condition | Selectivity, Cmol % Propionic acid productivity [g/h/kg_cat] | Carbon dioxide rate [g/h/kg_cat] | Water Gas Shift activity (proxy) [—] | Carbon balance [%] |
|---|---|---|---|---|---|
| Inv. Ex. 8 | 1 | 75.4 | 17.9 | 4.3 | 100.4 |
| Inv. Ex. 9 | 1 | 174.0 | 42.4 | 5.2 | 100.5 |
| Inv. Ex. 10 | 1 | 155.0 | 20.0 | 7.7 | 102.5 |
| Inv. Ex. 11 | 1 | 86.2 | 13.7 | 6.3 | 101.2 |
| Inv. Ex. 12 | 1 | 83.5 | 15.9 | 5.7 | 101.2 |
| Inv. Ex. 1 | 2 | 59.1 | 38.2 | 1.6 | 107.2 |
| Inv. Ex. 3 | 2 | 81.1 | 63.1 | 1.4 | 100.4 |
| Inv. Ex. 5 | 2 | 96.3 | 86.2 | 1.2 | 100.8 |
| Inv. Ex. 6 | 2 | 135.6 | 87.6 | 1.6 | 101.2 |
| Inv. Ex. 7 | 2 | 56.6 | 19.2 | 3.0 | 100.4 |
| Inv. Ex. 8 | 2 | 75.5 | 20.7 | 3.7 | 100.9 |
| Inv. Ex. 9 | 2 | 225.9 | 92.9 | 3.5 | 102.3 |

*Data is averaged of 2-8 hrs on stream

TABLE 5a

Catalytic Data for Comparative Examples 1-13

| Example | Condition | Ethylene Conversion, Cmol % | Selectivity, Cmol % Propionic acid | Ethane | 1-Propanol | Propionaldehyde | Methyl acetate |
|---|---|---|---|---|---|---|---|
| C. Ex. 1 | 1 | 24.5 | 98.4 | 0.7 | 0.0 | 0.3 | 0.0 |
| C. Ex. 2 | 1 | 1.2 | 92.0 | 2.6 | 0.2 | 3.7 | 0.1 |
| C. Ex. 3 | 1 | 0.8 | 87.5 | 3.7 | 0.6 | 3.1 | 0.5 |
| C. Ex. 4 | 1 | 1.3 | 78.3 | 11.0 | 1.2 | 4.6 | 0.9 |
| C. Ex. 5 | 1 | 0.9 | 89.4 | 3.4 | 0.5 | 3.3 | 0.5 |
| C. Ex. 6 | 1 | 2.6 | 94.9 | 1.3 | 0.7 | 1.1 | 0.1 |
| C. Ex. 7 | 1 | 4.9 | 97.7 | 1.3 | 0.1 | 0.5 | 0.0 |
| C. Ex. 8 | 1 | 6.2 | 97.6 | 1.0 | 0.0 | 0.8 | 0.0 |
| C. Ex. 9 | 1 | 0.2 | 2.1 | 48.2 | 4.7 | 23.2 | 2.4 |
| C. Ex. 10 | 1 | 0.4 | 0.4 | 50.1 | 22.0 | 19.8 | 1.3 |
| C. Ex. 11 | 1 | 0.4 | 0.6 | 50.0 | 13.1 | 25.6 | 1.7 |
| C. Ex. 12 | 1 | 0.3 | 0.7 | 80.2 | 4.1 | 7.9 | 1.3 |
| C. Ex. 13 | 1 | 13.6 | 0.3 | 82.9 | 1.3 | 1.5 | 0.7 |
| C. Ex. 2 | 2 | 1.1 | 88.1 | 5.9 | 0.6 | 4.3 | 0.2 |
| C. Ex. 3 | 2 | 0.6 | 74.4 | 10.4 | 3.0 | 5.1 | 1.8 |
| C. Ex. 4 | 2 | 0.5 | 21.7 | 43.0 | 8.8 | 9.3 | 2.6 |
| C. Ex. 5 | 2 | 0.6 | 73.5 | 11.3 | 2.8 | 5.0 | 1.7 |
| C. Ex. 6 | 2 | 2.3 | 93.7 | 2.9 | 0.3 | 1.5 | 0.2 |
| C. Ex. 8 | 2 | 6.4 | 96.6 | 1.7 | 0.1 | 0.9 | 0.0 |
| C. Ex. 9 | 2 | 0.2 | 2.0 | 56.8 | 4.4 | 18.0 | 4.2 |
| C. Ex. 10 | 2 | 0.6 | 1.2 | 35.1 | 16.9 | 35.4 | 2.2 |
| C. Ex. 11 | 2 | 0.4 | 1.3 | 42.5 | 8.5 | 36.3 | 2.3 |
| C. Ex. 12 | 2 | 0.2 | 1.6 | 73.6 | 5.4 | 10.7 | 2.5 |
| C. Ex. 13 | 2 | 15.3 | 0.3 | 85.7 | 1.0 | 1.2 | 0.1 |

TABLE 5b

Catalytic Data for Comparative Examples 1-13

| Example | Condition | Selectivity, Cmol % Ethyl acetate | Propyl acetate | 1-Methoxypropanel | 1-Ethoxypropane | Propylene | Propane |
|---|---|---|---|---|---|---|---|
| C. Ex. 1 | 1 | 0.0 | 0.4 | 0.0 | 0.2 | 0.0 | 0.0 |
| C. Ex. 2 | 1 | 0.0 | 0.8 | 0.0 | 0.6 | 0.0 | 0.0 |
| C. Ex. 3 | 1 | 0.5 | 1.7 | 0.1 | 2.2 | 0.2 | 0.0 |
| C. Ex. 4 | 1 | 1.3 | 1.8 | 0.2 | 0.8 | 0.0 | 0.0 |
| C. Ex. 5 | 1 | 0.6 | 1.5 | 0.2 | 0.5 | 0.1 | 0.0 |
| C. Ex. 6 | 1 | 0.1 | 1.1 | 0.2 | 0.4 | 0.0 | 0.0 |
| C. Ex. 7 | 1 | 0.1 | 0.3 | 0.0 | 0.2 | 0.0 | 0.0 |

TABLE 5b-continued

Catalytic Data for Comparative Examples 1-13

| Example | Condition | Selectivity, Cmol % Ethyl acetate | Propyl acetate | 1-Methoxypropanel | 1-Ethoxypropane | Propylene | Propane |
|---|---|---|---|---|---|---|---|
| C. Ex. 8 | 1 | 0.0 | 0.3 | 0.0 | 0.2 | 0.0 | 0.0 |
| C. Ex. 9 | 1 | 4.8 | 9.7 | 0.0 | 4.9 | 0.0 | 0.0 |
| C. Ex. 10 | 1 | 3.7 | 1.5 | 0.9 | 0.3 | 0.0 | 0.0 |
| C. Ex. 11 | 1 | 3.0 | 4.8 | 0.1 | 1.2 | 0.0 | 0.0 |
| C. Ex. 12 | 1 | 0.9 | 2.8 | 0.0 | 2.2 | 0.0 | 0.0 |
| C. Ex. 13 | 1 | 0.3 | 3.2 | 0.1 | 0.2 | 8.6 | 1.1 |
| C. Ex. 2 | 2 | 0.0 | 0.8 | 0.0 | 0.2 | 0.0 | 0.0 |
| C. Ex. 3 | 2 | 1.5 | 1.4 | 1.0 | 1.4 | 0.0 | 0.0 |
| C. Ex. 4 | 2 | 3.9 | 3.6 | 1.0 | 2.4 | 3.7 | 0.0 |
| C. Ex. 5 | 2 | 1.5 | 1.6 | 0.9 | 1.6 | 0.2 | 0.0 |
| C. Ex. 6 | 2 | 0.2 | 0.8 | 0.0 | 0.3 | 0.0 | 0.0 |
| C. Ex. 8 | 2 | 0.0 | 0.4 | 0.0 | 0.2 | 0.0 | 0.0 |
| C. Ex. 9 | 2 | 2.9 | 5.9 | 0.0 | 2.7 | 0.0 | 3.0 |
| C. Ex. 10 | 2 | 4.1 | 1.1 | 0.4 | 0.1 | 3.4 | 0.0 |
| C. Ex. 11 | 2 | 3.1 | 4.6 | 0.5 | 0.9 | 0.0 | 0.0 |
| C. Ex. 12 | 2 | 2.5 | 2.5 | 0.0 | 1.1 | 0.0 | 0.0 |
| C. Ex. 13 | 2 | 0.2 | 2.0 | 0.1 | 0.1 | 8.1 | 1.2 |

TABLE 5c

Catalytic Data for Comparative Examples 1-13

| Example | Condition | Propionic acid productivity [g/h/kg_cat] | Carbon dioxide rate ]g/h/kg_cat] | Water Gas Shift activity (proxy) [—] | Carbon balance [%] |
|---|---|---|---|---|---|
| C. Ex. 1 | 1 | 201.8 | 9.8 | 21.5 | 101.8 |
| C. Ex. 2 | 1 | 8.1 | 2.3 | 3.4 | 100.2 |
| C. Ex. 3 | 1 | 5.1 | 2.1 | 2.5 | 99.2 |
| C. Ex. 4 | 1 | 7.6 | 5.0 | 1.5 | 99.8 |
| C. Ex. 5 | 1 | 6.1 | 2.1 | 2.9 | 100.6 |
| C. Ex. 6 | 1 | 19.9 | 4.5 | 4.5 | 101.2 |
| C. Ex. 7 | 1 | 49.8 | 6.8 | 7.4 | 132.6 |
| C. Ex. 8 | 1 | 50.1 | 5.1 | 9.6 | 101.3 |
| C. Ex. 9 | 1 | 0.0 | 15.1 | 0.0 | 100.1 |
| C. Ex. 10 | 1 | 0.0 | 43.0 | 0.0 | 100.6 |
| C. Ex. 11 | 1 | 0.0 | 35.0 | 0.0 | 100.6 |
| C. Ex. 12 | 1 | 0.0 | 29.2 | 0.0 | 100.6 |
| C. Ex. 13 | 1 | 0.3 | 302.8 | 0.0 | 99.6 |
| C. Ex. 2 | 2 | 6.9 | 3.2 | 2.2 | 100.0 |
| C. Ex. 3 | 2 | 2.8 | 2.7 | 1.0 | 98.2 |
| C. Ex. 4 | 2 | 0.7 | 6.2 | 0.1 | 97.1 |
| C. Ex. 5 | 2 | 3.1 | 2.6 | 1.2 | 100.0 |
| C. Ex. 6 | 2 | 16.8 | 5.0 | 3.3 | 100.1 |
| C. Ex. 8 | 2 | 50.1 | 8.3 | 6.0 | 100.3 |
| C. Ex. 9 | 2 | 0.0 | 16.0 | 0.0 | 99.9 |
| C. Ex. 10 | 2 | 0.0 | 36.5 | 0.0 | 100.4 |
| C. Ex. 11 | 2 | 0.0 | 32.2 | 0.0 | 100.5 |
| C. Ex. 12 | 2 | 0.0 | 27.6 | 0.0 | 100.6 |
| C. Ex. 13 | 2 | 0.3 | 302.6 | 0.0 | 99.5 |

TABLE 6a

Catalytic Data for Inventive Examples 13-19

| Example | Condition | Ethylene Conversion, Cmol % | Selectivity, Cmol % Propionic acid | Ethane | 1-Propanol | Propionaldehyde | Methyl acetate |
|---|---|---|---|---|---|---|---|
| Inv. Ex. 13 | 3 | 12.5 | 94.8 | 0.8 | 0.0 | 0.0 | 1.2 |
| Inv. Ex. 14 | 3 | 9.4 | 96.8 | 0.5 | 0.0 | 0.0 | 0.9 |
| Inv. Ex. 15 | 3 | 8.9 | 90.5 | 2.1 | 0.0 | 0.0 | 3.5 |
| Inv. Ex. 16 | 3 | 9.6 | 96.3 | 0.9 | 0.0 | 0.0 | 0.8 |
| Inv. Ex. 17 | 3 | 13.8 | 95.5 | 0.9 | 0.0 | 0.0 | 1.4 |

TABLE 6a-continued

| Catalytic Data for Inventive Examples 13-19 | | | | | | | | |
|---|---|---|---|---|---|---|---|---|
| | | Ethylene | Selectivity, Cmol % | | | | | |
| Example | Condition | Conversion, Cmol % | Propionic acid | Ethane | 1-Propanol | Propionaldehyde | Methyl acetate |
| Inv. Ex. 18 | 3 | 9.6 | 90.2 | 4.7 | 0.0 | 1.6 | 0.0 |
| Inv. Ex. 19 | 3 | 9.3 | 92.6 | 1.5 | 0.0 | 0.0 | 2.3 |
| Inv. Ex. 13 | 4 | 22.6 | 97.0 | 1.4 | 0.0 | 0.0 | 0.8 |
| Inv. Ex. 14 | 4 | 8.1 | 95.3 | 1.9 | 0.1 | 0.1 | 1.8 |
| Inv. Ex. 15 | 4 | 11.5 | 89.1 | 5.1 | 0.1 | 0.1 | 4.0 |
| Inv. Ex. 16 | 4 | 8.5 | 96.6 | 1.7 | 0.1 | 0.1 | 0.6 |
| Inv. Ex. 17 | 4 | 12.2 | 93.3 | 3.0 | 0.0 | 0.1 | 2.5 |
| Inv. Ex. 18 | 4 | 9.3 | 91.9 | 5.5 | 0.1 | 1.5 | 0.0 |
| Inv. Ex. 19 | 4 | 10.3 | 94.5 | 2.0 | 0.1 | 0.1 | 2.1 |
| Inv. Ex. 13 | 5 | 41.3 | 96.7 | 2.3 | 0.0 | 0.0 | 0.6 |
| Inv. Ex. 14 | 5 | 10.2 | 93.8 | 3.6 | 0.0 | 0.0 | 2.0 |
| Inv. Ex. 15 | 5 | 12.3 | 85.1 | 9.5 | 0.1 | 0.2 | 3.8 |
| Inv. Ex. 16 | 5 | 6.6 | 92.4 | 4.2 | 0.1 | 0.1 | 2.3 |
| Inv. Ex. 17 | 5 | 10.2 | 86.8 | 8.0 | 0.1 | 0.2 | 4.2 |
| Inv. Ex. 18 | 5 | 9.5 | 88.6 | 9.1 | 0.1 | 1.5 | 0.1 |

TABLE 6b

| Catalytic Data for Inventive Examples 13-19 | | | | | | | |
|---|---|---|---|---|---|---|---|
| | | Selectivity, Cmol % | | | | | |
| Example | Condition | Ethyl acetate | Propyl acetate | 1-Methoxypropanel | 1-Ethoxypropane | Propylene | Propane |
| Inv. Ex. 13 | 3 | 0.1 | 0.1 | 1.7 | 1.3 | 0.0 | 0.0 |
| Inv. Ex. 14 | 3 | 0.0 | 0.3 | 0.6 | 0.8 | 0.0 | 0.0 |
| Inv. Ex. 15 | 3 | 0.1 | 0.2 | 0.3 | 3.3 | 0.0 | 0.0 |
| Inv. Ex. 16 | 3 | 0.1 | 0.0 | 0.8 | 1.1 | 0.0 | 0.0 |
| Inv. Ex. 17 | 3 | 0.1 | 0.1 | 0.1 | 2.0 | 0.0 | 0.0 |
| Inv. Ex. 18 | 3 | 0.1 | 0.1 | 1.6 | 1.6 | 0.0 | 0.0 |
| Inv. Ex. 19 | 3 | 0.2 | 0.1 | 0.1 | 3.2 | 0.0 | 0.0 |
| Inv. Ex. 13 | 4 | 0.0 | 0.1 | 0.4 | 0.1 | 0.0 | 0.0 |
| Inv. Ex. 14 | 4 | 0.2 | 0.1 | 0.3 | 0.2 | 0.0 | 0.0 |
| Inv. Ex. 15 | 4 | 0.1 | 0.3 | 0.0 | 1.3 | 0.0 | 0.0 |
| Inv. Ex. 16 | 4 | 0.1 | 0.1 | 0.3 | 0.4 | 0.0 | 0.0 |
| Inv. Ex. 17 | 4 | 0.1 | 0.1 | 0.0 | 0.8 | 0.0 | 0.0 |
| Inv. Ex. 18 | 4 | 0.2 | 0.1 | 0.3 | 0.5 | 0.0 | 0.0 |
| Inv. Ex. 19 | 4 | 0.0 | 0.1 | 0.1 | 1.1 | 0.0 | 0.0 |
| Inv. Ex. 13 | 5 | 0.0 | 0.3 | 0.0 | 0.0 | 0.0 | 0.0 |
| Inv. Ex. 14 | 5 | 0.1 | 0.2 | 0.1 | 0.1 | 0.0 | 0.0 |
| Inv. Ex. 15 | 5 | 0.4 | 0.5 | 0.0 | 0.5 | 0.0 | 0.0 |
| Inv. Ex. 16 | 5 | 0.3 | 0.2 | 0.1 | 0.3 | 0.0 | 0.0 |
| Inv. Ex. 17 | 5 | 0.1 | 0.2 | 0.0 | 0.4 | 0.0 | 0.0 |
| Inv. Ex. 18 | 5 | 0.3 | 0.1 | 0.1 | 0.2 | 0.0 | 0.0 |

TABLE 6c

| Catalytic Data for Inventive Examples 13-19 | | | | | |
|---|---|---|---|---|---|
| | | Selectivity, Cmol % | | | |
| Example | Condition | Propionic acid productivity [g/h/kg_cat] | Carbon dioxide rate [g/h/kg_cat] | Water Gas Shift activity (proxy) [—] | Carbon balance [%] |
| Inv. Ex. 13 | 3 | 101.5 | 16.1 | 6.5 | 100.7 |
| Inv. Ex. 14 | 3 | 80.6 | 8.1 | 10.0 | 103.6 |
| Inv. Ex. 15 | 3 | 66.8 | 28.3 | 2.4 | 99.3 |
| Inv. Ex. 16 | 3 | 77.7 | 5.3 | 14.7 | 101.1 |
| Inv. Ex. 17 | 3 | 114.6 | 17.4 | 6.6 | 101.3 |
| Inv. Ex. 18 | 3 | 69.5 | 11.9 | 6.2 | 99.2 |
| Inv. Ex. 19 | 3 | 72.0 | 21.2 | 3.7 | 99.3 |
| Inv. Ex. 13 | 4 | 195.7 | 29.0 | 6.7 | 102.7 |
| Inv. Ex. 14 | 4 | 65.0 | 15.5 | 4.2 | 100.6 |

TABLE 6c-continued

Catalytic Data for Inventive Examples 13-19

| Example | Condition | Selectivity, Cmol % | | | |
|---|---|---|---|---|---|
| | | Propionic acid productivity [g/h/kg_cat] | Carbon dioxide rate [g/h/kg_cat] | Water Gas Shift activity (proxy) [—] | Carbon balance [%] |
| Inv. Ex. 15 | 4 | 86.2 | 44.4 | 2.0 | 100.3 |
| Inv. Ex. 16 | 4 | 67.3 | 8.6 | 7.8 | 100.8 |
| Inv. Ex. 17 | 4 | 98.1 | 32.5 | 3.0 | 101.4 |
| Inv. Ex. 18 | 4 | 70.4 | 12.5 | 9.4 | 102.5 |
| Inv. Ex. 19 | 4 | 83.0 | 26.9 | 3.1 | 100.2 |
| Inv. Ex. 13 | 5 | 393.2 | 60.5 | 6.5 | 106.9 |
| Inv. Ex. 14 | 5 | 82.2 | 28.5 | 2.9 | 100.9 |
| Inv. Ex. 15 | 5 | 87.0 | 71.8 | 1.2 | 100.4 |
| Inv. Ex. 16 | 5 | 49.1 | 15.6 | 3.1 | 100.0 |
| Inv. Ex. 17 | 5 | 72.5 | 71.4 | 1.0 | 100.0 |
| Inv. Ex. 18 | 5 | 68.1 | 15.8 | 4.4 | 98.6 |

What is claimed is:

1. A gas phase process for producing a carboxylic acid or an alkyl ester comprising:

(a) providing a catalyst support comprising deposits of cobalt thiocyanate on at least a portion of the catalyst support, wherein the catalyst support has a surface area of greater than 5 $m^2/g$;

(b) heating the catalyst support to convert the cobalt thiocyanate on the support to cobalt sulfide to form a supported cobalt sulfide catalyst; and (c) reacting alkene gas, steam or an alkanol gas, and a carbon-containing gas in the presence of the supported cobalt sulfide catalyst in a reactor to form a product stream, wherein the carbon-containing gas comprises carbon monoxide or a mixture of carbon monoxide and carbon dioxide, wherein when steam is used as a reactant, the product stream comprises a carboxylic acid, and wherein when alkanol gas is used as a reactant, the product stream comprises an alkyl ester.

2. The process of claim 1, wherein the catalyst support comprising deposits of cobalt thiocyanate on at least a portion of the catalyst support is formed by contacting an aqueous solution of cobalt (II) salt in the presence of thiocyanate anion with a catalyst support to deposit the aqueous solution on at least a portion of the catalyst support.

3. The process of claim 1 further comprising dissolving cobalt thiosulfate in water to provide the aqueous solution of cobalt (II) salt in the presence of thiocyanate anion.

4. The process of claim 1, wherein the aqueous solution does not include more than 0.1 molar equivalents of cations other than cobalt (II) relative to cobalt, and wherein the aqueous solution does not include more than 0.1 molar equivalents of anions other than thiocyanate anion relative to thiocyanate.

5. The process of claim 1, wherein the catalyst support is heated at a temperature between 200° C. and 550° C.

6. The process of claim 1, further comprising drying the catalyst support comprising deposits of cobalt thiocyanate on at least a portion of the catalyst support under inert conditions at a temperature of 150° C. or less prior to heating the catalyst support in step (b).

7. The process of claim 1, further comprising passivating the supported cobalt sulfide catalyst with a diluted oxygen stream comprising up to 2 volume percent $O_2$ at a temperature of 25° C. or less.

8. The process of claim 1, wherein the cobalt sulfide comprises $CoS_2$, $Co_4S_3$, $Co_3S_4$, COS, $Co_7S_8$, $Co_9S_8$, $Co_{1-x}S$ where x is less than or equal to 0.2, or combinations thereof.

9. The process of claim 1, wherein the bulk sulfur-to-cobalt atomic ratio is equal or greater than 0.3.

10. The process of claim 1, wherein the catalyst support comprises alumina, carbon, silicon carbide, silica, silica-alumina, halfnia, zirconia, titania, or mixtures thereof, or wherein the cobalt content in the supported cobalt sulfide catalyst is between 5 weight percent and 50 weight percent, based on the total weight of the supported cobalt sulfide catalyst.

11. The process of claim 1, wherein the surface area of the catalyst support is greater than 10 $m^2/g$ and up to 800 $m^2/g$.

12. The process of claim 1, wherein the catalyst support is heated to convert the cobalt thiocyanate on the support to cobalt sulfide to form a supported cobalt sulfide catalyst outside the reactor, and wherein the process further comprises adding the supported cobalt sulfide catalyst to the reactor.

13. The process of claim 1, wherein the catalyst support is heated in the reactor to convert the cobalt thiocyanate on the support to cobalt sulfide to form a supported cobalt sulfide catalyst.

14. The process of claim 1, wherein the carboxylic acid selectivity or the alkyl ester selectivity is equal to or greater than 80 mol %.

15. The process of claim 1, wherein the alkene gas is ethylene, or wherein the process is continuous.

* * * * *